US006607499B1

(12) United States Patent
Becher

(10) Patent No.: US 6,607,499 B1
(45) Date of Patent: Aug. 19, 2003

(54) PORTABLE REAL TIME, DRY MECHANICAL RELAXATION AND PHYSICAL THERAPY DEVICE SIMULATING APPLICATION OF MASSAGE AND WET HYDROTHERAPY FOR LIMBS

(76) Inventor: James Becher, 437 Carlls Path, Deer Park, NY (US) 11729

( * ) Notice: Subject to any disclaimer, the term of this patent is extended or adjusted under 35 U.S.C. 154(b) by 0 days.

(21) Appl. No.: 09/552,724

(22) Filed: Apr. 19, 2000

(51) Int. Cl.[7] ................................................ A61M 7/00

(52) U.S. Cl. ......................... 601/133; 601/97; 601/101; 601/103

(58) Field of Search ........................... 601/133, 23, 24, 601/26–31, 34–36, 1, 84, 97–99, 101–105, 112–116, 125–127

(56) References Cited

U.S. PATENT DOCUMENTS 1,161,767 A * 11/1915 Geraldine .................. 601/118
1,612,899 A * 1/1927 Ahlgren
3,945,637 A * 3/1976 Simjian ...................... 482/62
4,009,710 A 3/1977 Inada ......................... 128/44
4,013,069 A 3/1977 Hasty ...................... 128/24 R
4,023,566 A 5/1977 Martinmass ................ 128/33
4,026,299 A 5/1977 Sauder ...................... 128/400
4,041,938 A 8/1977 Wintoniw ..................... 128/52
4,047,377 A 9/1977 Banks ...................... 58/152 B
4,055,170 A 10/1977 Nohmura ..................... 128/33
4,079,732 A 3/1978 Fujimoto ..................... 128/55
4,082,918 A 4/1978 Chang ..................... 179/1 AA
4,118,946 A 10/1978 Tubin ....................... 62/514 R
4,124,022 A 11/1978 Gross ......................... 128/1 C
4,139,001 A 2/1979 Macabee ..................... 128/64
4,141,585 A 2/1979 Blackman ................... 297/180
4,149,531 A 4/1979 Tanaka ...................... 128/152
4,149,541 A 4/1979 Gammons ................... 128/400
4,157,712 A 6/1979 Gaynor ....................... 128/57
4,169,466 A 10/1979 Wong .......................... 128/57
4,184,537 A 1/1980 Sauder ........................ 165/46
4,198,962 A 4/1980 McCauley ................... 128/33
4,217,705 A 8/1980 Donzis .......................... 39/29
4,231,355 A 11/1980 Hara ......................... 128/24.2
4,233,966 A 11/1980 Takahashi .................... 128/67
4,255,989 A 3/1981 Dinelli ........................ 74/831
4,258,706 A 3/1981 Shank ......................... 128/33
4,315,502 A 2/1982 Gorges ....................... 128/1 C
4,339,833 A 7/1982 Mandell ........................ 4/542
4,353,359 A 10/1982 Milbauer ..................... 128/66
4,373,516 A 2/1983 Masuda ....................... 128/57
4,383,342 A 5/1983 Forster .......................... 5/432
4,396,010 A 8/1983 Arkans ..................... 128/24 R
4,412,535 A 11/1983 Teren .......................... 128/57
4,422,448 A 12/1983 Sugai .......................... 128/44
4,422,449 A 12/1983 Hamabe ...................... 128/44
4,428,368 A 1/1984 Torii ........................... 128/38
4,432,355 A 2/1984 Delluc ......................... 128/56
4,454,867 A 6/1984 Swanson ..................... 128/57

(List continued on next page.)

*Primary Examiner*—Justine R. Yu
(74) *Attorney, Agent, or Firm*—Alfred M. Walker

(57) ABSTRACT

A relaxation station for inducing user relaxation includes a sleeve with a reclining surface attached to said frame for accommodating a limb of a user. The sleeve has a plurality of preferably pairs of massage grippers connected to and extending generally upward therefrom. These massage gripper pairs are elongated members projecting generally upward from the sleeve and the gripper pairs are capable of moving reciprocally between an open and a closed position to simulate finger manipulated massage. In a closed position, they cradle and contact the body or a portion thereof of a user. These massage gripper pairs having motive actuators for producing movement between said open and said closed positions, such as scissors extenders or flexible cables The massage gripper elongated members produce massage motions in at least one massage contact pad. The contact pads preferably have a temperature regulator and a dry hydrotherapy supply for enhancing the relaxation of a user and to simulate human massage.

6 Claims, 19 Drawing Sheets

U.S. PATENT DOCUMENTS

| | | | | | |
|---|---|---|---|---|---|
| 4,478,214 | A | | 10/1984 | Lamont | 128/149 |
| 4,513,738 | A | | 4/1985 | Niessen | 128/57 |
| 4,523,340 | A | | 6/1985 | Watkins | 4/542 |
| 4,548,357 | A | | 10/1985 | Schmidt | 239/289 |
| 4,553,534 | A | | 11/1985 | Stiegler | 128/24.1 |
| 4,573,449 | A | | 3/1986 | Warnke | 128/1 C |
| 4,574,786 | A | | 3/1986 | Hashimoto | 128/52 |
| 4,576,149 | A | | 3/1986 | Otuka | 128/33 |
| 4,577,625 | A | | 3/1986 | Lohati | 128/57 |
| 4,586,493 | A | | 5/1986 | Goodman | 128/57 |
| 4,607,405 | A | | 8/1986 | Ellis | 5/451 |
| 4,615,336 | A | | 10/1986 | Fijimoto | 128/52 |
| 4,633,858 | A | * | 1/1987 | Rutsch et al. | 128/59 |
| 4,634,179 | A | | 1/1987 | Hashimoto | 297/284 |
| 4,635,620 | A | | 1/1987 | Ricchio | 128/64 |
| 4,640,266 | A | | 2/1987 | Levy | 128/1 R |
| 4,640,267 | A | | 2/1987 | Lawson | 128/1 R |
| 4,655,505 | A | | 4/1987 | Kashiwamura | 297/284 |
| 4,656,998 | A | | 4/1987 | Masuda | 128/57 |
| 4,688,556 | A | | 8/1987 | Keller | 128/57 |
| 4,713,853 | A | | 12/1987 | Ricchio | 5/451 |
| 4,718,408 | A | | 1/1988 | Barreiro | 128/52 |
| 4,721,000 | A | | 1/1988 | Hengl | 128/57 |
| 4,736,800 | A | | 4/1988 | Rohner | 168/18 |
| 4,738,119 | A | | 4/1988 | Zafred | 62/259.3 |
| 4,744,281 | A | | 5/1988 | Isozaki | 84/1.28 |
| 4,747,408 | A | | 5/1988 | ChuanChih | 128/400 |
| 4,751,919 | A | | 6/1988 | Thomsen | 128/66 |
| 4,757,562 | A | | 7/1988 | Mützell | 4/615 |
| 4,757,808 | A | | 7/1988 | Effler | 128/66 |
| 4,762,121 | A | | 8/1988 | Shienfeld | 128/64 |
| 4,762,131 | A | | 8/1988 | Okuda | 128/396 |
| 4,763,428 | A | | 8/1988 | Fischer | 40/152 |
| 4,779,615 | A | * | 10/1988 | Frazier | 128/33 |
| 4,785,797 | A | | 11/1988 | Cuervo | 128/33 |
| 4,793,328 | A | | 12/1988 | Kolstedt | 128/24 R |
| 4,794,991 | A | | 1/1989 | Honderich | 168/26 |
| 4,796,616 | A | | 1/1989 | Panahpour | 128/57 |
| 4,804,977 | A | | 2/1989 | Long | 346/76 L |
| 4,846,525 | A | | 7/1989 | Manning | 297/180 |
| 4,853,988 | A | | 8/1989 | Mützell | 297/180 |
| 4,854,502 | A | | 8/1989 | Cox | 239/124 |
| 4,865,020 | A | | 9/1989 | Bullard | 128/64 |
| 4,875,470 | A | | 10/1989 | Cotone | 128/57 |
| 4,936,294 | A | | 6/1990 | Chu | 128/57 |
| 4,943,117 | A | | 7/1990 | Brown | 297/392 |
| 4,974,582 | A | | 12/1990 | Johnson | 128/60 |
| 4,976,256 | A | | 12/1990 | Marlin | 128/64 |
| 4,981,010 | A | | 1/1991 | Orza | 54/82 |
| 4,981,131 | A | | 1/1991 | Hazard | 128/38 |
| 4,997,506 | A | | 3/1991 | Recher | 156/235 |
| 5,018,511 | A | * | 5/1991 | Yokoi | 601/84 |
| 5,020,517 | A | | 6/1991 | Foster | 129/33 |
| 5,020,518 | A | | 6/1991 | Spears | 128/52 |
| 5,024,650 | A | | 6/1991 | Hagiwara | 600/26 |
| 5,046,004 | A | | 9/1991 | Tsumura | 364/419 |
| 5,074,286 | A | | 12/1991 | Gillaspie | 128/33 |
| 5,083,491 | A | | 1/1992 | Fields | 84/21 |
| 5,083,552 | A | | 1/1992 | Lipowitz | 128/44 |
| 5,097,821 | A | | 3/1992 | Eakin | 128/33 |
| 5,113,851 | A | | 5/1992 | Gamba | 128/33 |
| 5,125,175 | A | | 6/1992 | Huff | 40/152 |
| 5,137,016 | A | | 8/1992 | Yamasaki | 128/52 |
| 5,142,961 | A | | 9/1992 | Paroutaud | 84/726 |
| 5,143,055 | A | | 9/1992 | Eakin | 128/33 |
| 5,153,829 | A | | 10/1992 | Furuya | 364/419 |
| 5,167,227 | A | * | 12/1992 | Meserlian | 128/64 |
| 5,184,365 | A | | 2/1993 | Stafford | 5/632 |
| 5,186,519 | A | | 2/1993 | Larson | 297/443 |
| 5,188,096 | A | | 2/1993 | Yoo | 128/33 |
| 5,208,421 | A | | 5/1993 | Lisle | 84/645 |
| 5,211,162 | A | | 5/1993 | Gillen | 128/64 |
| 5,247,126 | A | | 9/1993 | Okamura | 84/609 |
| 5,247,925 | A | | 9/1993 | Yamasaki | 128/33 |
| 5,262,940 | A | | 11/1993 | Sussman | 364/403 |
| 5,265,590 | A | | 11/1993 | Takagi | 128/33 |
| 5,266,070 | A | | 11/1993 | Hagiwara | 600/27 |
| 5,267,942 | A | | 12/1993 | Saperston | 600/28 |
| 5,281,499 | A | | 1/1994 | Bussard | 430/1 |
| 5,289,438 | A | | 2/1994 | Gall | 369/4 |
| 5,304,112 | A | | 4/1994 | Mrklas | 600/27 |
| 5,307,574 | A | | 5/1994 | Huff | 40/152 |
| 5,317,732 | A | | 5/1994 | Gerlach | 395/600 |
| 5,329,381 | A | | 7/1994 | Payne | 358/455 |
| 5,352,181 | A | | 10/1994 | Davis | 600/28 |
| 5,352,186 | A | | 10/1994 | Yamasaki | 601/99 |
| 5,356,368 | A | | 10/1994 | Monroe | 600/68 |
| 5,368,359 | A | | 11/1994 | Eakin | 297/217 |
| 5,377,024 | A | | 12/1994 | Dillinger | 358/502 |
| 5,387,181 | A | | 2/1995 | Olsen | 601/155 |
| 5,388,264 | A | | 2/1995 | Tobias | 395/650 |
| 5,389,493 | A | | 2/1995 | Asai | 430/211 |
| 5,390,138 | A | | 2/1995 | Milne | 381/119 |
| 5,393,926 | A | | 2/1995 | Johnson | 84/610 |
| 5,403,263 | A | | 4/1995 | Rodgers | 600/28 |
| 5,425,699 | A | | 6/1995 | Speigel | 600/26 |
| 5,437,608 | A | | 8/1995 | Cutler | 601/49 |
| 5,441,997 | A | | 8/1995 | Walsh | 524/147 |
| 5,459,282 | A | | 10/1995 | Willis | 84/645 |
| 5,460,598 | A | | 10/1995 | Yamasaki | 601/49 |
| 5,460,871 | A | | 10/1995 | Andersen | 428/287 |
| 5,462,516 | A | | 10/1995 | Anderson | 601/99 |
| 5,487,590 | A | | 1/1996 | Haynes | 297/344.14 |
| 5,503,618 | A | | 4/1996 | Rey | 601/15 |
| 5,540,651 | A | | 7/1996 | Risch | 601/148 |
| D372,802 | S | | 8/1996 | Fujimoto | 106/367 |
| 5,637,076 | A | | 6/1997 | Hazard | 601/5 |
| 5,653,679 | A | | 8/1997 | Belanchi | 601/98 |
| 5,676,633 | A | | 10/1997 | August | 600/27 |
| 5,695,455 | A | | 12/1997 | Alton | 601/47 |
| 5,741,218 | A | | 4/1998 | Fujii | 601/90 |
| 5,762,618 | A | | 6/1998 | Yamanaka | 601/148 |
| 5,779,652 | A | | 7/1998 | Mencher-Aliazzo | 601/132 |
| D397,259 | S | | 8/1998 | Chatani | D6/367 |
| 5,792,080 | A | | 8/1998 | Ookawa | 601/115 |
| 5,792,081 | A | * | 8/1998 | Cross | 601/123 |
| 5,792,082 | A | | 8/1998 | Yamanaka | 601/148 |
| 5,813,727 | A | | 9/1998 | Sugawa | 297/411.42 |
| 5,827,206 | A | | 10/1998 | Lunter | 601/148 |
| 5,836,645 | A | | 11/1998 | Sakaue | 297/68 |
| D402,479 | S | | 12/1998 | Inada | D6/361 |
| 5,843,006 | A | * | 12/1998 | Phillips et al. | 601/133 |
| 5,864,868 | A | | 1/1999 | Contois | 707/104 |
| 5,868,687 | A | | 2/1999 | Tedesco | 601/49 |
| 5,904,660 | A | | 5/1999 | Kim | 601/108 |
| 6,077,293 | A | * | 6/2000 | King | 606/237 |
| 6,174,298 | B1 | * | 1/2001 | Quinn et al. | 601/137 |
| 6,190,339 | B1 | * | 2/2001 | Imazaike et al. | 601/133 |
| 6,200,282 | B1 | * | 3/2001 | Furuie et al. | 601/98 |

* cited by examiner

*Power Control Relays*

1. LEG TRUSS UP/DOWN
2. AUDIO SYSTEM
3. FIBEROPTIC LAMPS
4. AROMATHERAPY
5. NEGATIVE IONIZERS
6. BODY FINGERS HEAT
7. FEET HEAT CONTROL
8. HYDRO HEAT CONTROL

PORTABLE REAL TIME, DRY MECHANICAL RELAXATION AND PHYSICAL THERAPY DEVICE SIMULATING APPLICATION OF MASSAGE AND WET HYDROTHERAPY FOR LIMBS

This application is based upon Disclosure Document No. 464469, filed Nov. 1, 1999.

BACKGROUND OF THE INVENTION

This invention relates to relaxation and therapeutic massage apparatuses and, more particularly, to an integrated multi-functional system housed in one ergonomically designed enclosure. The dry, mechanical system closely simulates therapeutic massage provided by manual manipulation of a human massage provider and/or a wet, water-.based hydrotherapy device.

DESCRIPTION OF THE RELATED ART

As the work environment and the complexity of contemporary human interaction are increasingly influenced by technologies such as the use of computers and telecommunications devices, incidences of acute stress are more prevalent. Rejuvenation of the individual through stress relief methods is frequently sought since rest alone is often inadequate to the task. The prior art has addressed stress relief with several devices, systems and methods. The prior art also includes conventional hand-provided massage by a physical therapist or masseuse. However, most simulated massage systems are harshly vibratory and dry, and can irritate injured muscles without providing significant relief, especially for persons with head and neck related injuries such as temporal mandibular joint (TMJ) syndrome.

Moreover, devices which attempt to soften treatment with water filled conduits require complex water pumps. Therefore, there is a need for a simulated massage device which can simulate soft finger and knuckle-applied massage without the use of harsh vibrations of certain mechanical massagers and which can provide simulated water-based hydrotherapy without use of expensive water filled conduits.

Some exemplary patents use mechanical devices to provide massage of various body parts. McCauly (U.S. Pat. No. 4,198,962) describes a foot massager using a plurality of balls attached to a frame engaged with a vibrator. Sugawa et al. (U.S. Pat. No. 5,813,727) relates to a massaging chair with an adjustable reclining mechanism and a mechanical back massage element. Yamasaki et al. (U.S. Pat. No. 5,352,186) is a finger pressure device built into the back of a chair. Using a motor driven long-stroke linear actuator, it drives two wheels up and down the user's spine.

Belanchi's (U.S. Pat. No. 5,653,679) massaging machine uses a motor driven disk to oscillate a plurality of spring biased mechanical fingers built into a chair back to simulate the finger massage of a user's back by a skilled masseur. The prior art also represents attempts to provide massage using fluid techniques. Torii (U.S. Pat. No. 4,428,368) has a massage device driven by a motor which uses the cyclic application of vacuum to various body areas by hose-connected suction cups. This action simulates manual kneading action. In addition, heat and/or low frequency electrical pulses can be applied to the vacuum stimulated sites.

Meserlain (U.S. Pat. No. 5,167,227) details an apparatus for massaging the legs of a horse. A flexible wrap-around pad with hose imbedded in the inner surface is wrapped around the horse's leg and straps are used to secure it in place. Water is circulated through the hose by pumping it from a tank in a closed circuit. An air pump is used to introduce compressed air into the inlet water stream mixing with it to provide a massaging action in addition to a cooling action by controlling the tank water temperature.

Arkans (U.S. Pat. No. 4,396,010) describes a sequential pressure device that has the ability of supplying a sequential wave of cyclic compressive pressure against a patient's limb by virtue of a multi-chambered air tight sleeve that is attached to a controlled source of compressed air controlled by the cycling of solenoid valves.

Risch et al. (U.S. Pat. No. 5,540,651) describe a waterproof hydrotherapy bed. Using a gel-filled double layer top membrane to reduce acoustic noise, the user lies upon the bed while pressurized liquid jets impinge from below. A hand-held control pod interacts with a control computer to influence the operation of the linear actuator which moves the array of liquid jets.

Lunter (U.S. Pat. No. 5,827,206) presents a dry hydromassage chair wherein fluid jets are directed to impinge upon a membrane separating the fluid from the spinal area of the user.

Ricchio (U.S. Pat. No. 4,713,853) describes an apparatus for improved water therapy wherein a person is buoyantly supported in a prone position on a top membrane of a waterbed mattress containing heated water. Arrays of water jets within the mattress impinge on the underside of the top membrane. By mixing air with the water stream, "softer" aspirated jets impinge on the user.

Other prior art patents use alternate means to enhance relaxation. Eakin's (U.S. Pat. No. 5,143,055) somatic acoustic chair incorporates a rigid framework with a resilient support liner to expose the user to vibrations from sound emanating from loudspeakers within.

Hagiwara et al. (U.S. Pat. No. 5,266,070) describes a relaxation refreshment apparatus. This is a reclining chair apparatus which uses vibratory, optical, pneumatic, aromatic and acoustic stimuli to help the user to quickly recover from mental fatigue. Controlling these stimuli in a closed-loop feedback fashion by sensing skin electrical resistance or ECG signals, the user need not take an active role in controlling the relaxation program.

Lipowitz (U.S. Pat. No. 5,083,552) relates to a computer controlled massage device. While this device is related to the mechanical massage devices mentioned earlier, the implementation as a robotic arm with three degrees of freedom that can massage the entire body under computer control makes it qualitatively different.

Mrklas et al. (U.S. Pat. No. 5,304,112) in her stress reduction system and method uses soothing audio, visual and other sensory effects to reduce stress. Using projection of images on a curved screen, laser image generation, computer control and biofeedback techniques, the method also allows for the use of a human operator interacting with the user via an operator's console.

The present invention has some functions such as mechanical and dry hydromassage which bear some resemblance to prior art, however the apparatus is distinguished. The comprehensive integrated nature of the present invention and its reliance on computer control bears some similarity to other prior art, in this case the operational methods differ and the implementation details of the apparatus are also distinguished.

In addition, the configuration of the massaging motive components, in conjunction with a dry hydrotherapy component, closely simulates human-provided massage without harsh side effects. In addition, the present invention avoids the use of complex software by controlling movement of motive gripping elements (simulating finger massage) with musical instrument digital interface (MIDI) controllers. These MIDI controllers can also control the rhythmic activation of the flow of air bubbles in tubes and a layer of temperature controlled resistive wire adjacent to the motive gripping elements.

OBJECTS OF THE INVENTION

It is therefore an object of the present invention to incorporate gripper mechanisms with integral heaters to perform deep massage of the limbs.

It is a further object of the present invention to provide dry hydrotherapy with heat and actual water channels.

It is also an object of the present invention to provide vibratory stimulation through the use of wave-like interference patterns of two motor-driven eccentric weights.

It is another object of the present invention to provide a modified Shiatzu massage using wooden balls which spin and move orbitally.

It is yet still another object of this invention to use musical instrument digital interface (MIDI) controlled actuation of grippers and other system actuators by simply mapping their control interfaces as musical notes, thereby avoiding the use of specialized software for control.

It is also an object of this invention to integrate these features and others in an ergonomic relaxation station.

It is another object of this invention to provide a modular deep massage unit incorporating grippers and dry hydrotherapy for treating various limbs of the human or animal body.

It is yet another object of the present invention to improve over the disadvantages of the prior art.

SUMMARY OF THE INVENTION

In keeping with these objects and others which may become apparent, the present invention provides for a relaxation device for inducing user relaxation. The device may be either an open sleeve for treating an individual limb, such as a hand, foot or part of an arm or a leg, or it may be an integrated station for the whole body to lie in.

In contrast to the prior art, the present invention closely simulates human hand-applied massage by a plurality of massage grippers that simulate rhythmic kneading by fingers without unnecessary and aggravating vibrations, preferably in conjunction with a pulsating flow of air bubbles in fluid-filled tubes and a layer of temperature controlled resistive wire which are adjacent to the grippers, to simulate either actual water-based hydrotherapy or the warm, blood flow induced feeling of actual hand-applied massage.

For the full body device, a couch has a frame and a reclining surface attached to the frame for accommodating a user in a reclining position. This frame includes a plurality of pairs of massage grippers connected to and extending generally upward therefrom, to simulate fingers applying a gripping massage technique.

These massage gripper pairs are elongated members projecting generally upward from the frame. These gripper pairs are capable of moving reciprocally between an open and a closed position, for cradling and contacting the body of a user.

The massage gripper pairs are controlled by motive actuators that produce movement between the open and closed positions.

The massage gripper elongated members respectively have respectively attached thereon one or more soft massage contact pads that simulate fingertips and which contact and massage the body of a user.

Each contact pad includes a super-soft outer shell surrounding and attached to a relatively harder resilient inner liner, which in turn is attached to the elongated gripper member.

These pads simulate fingertips, wherein the soft outer shell simulates the skin and outer tissues, but the harder inner layer simulates the inner tissues, cartilage and bones of the finger.

The motive actuators of the massage gripper elongated members are connected to produce open and closed massage motions in the massage contact pads.

The motive actuators for the massage gripper members may be by scissors extender linkages, or by flexible cables or other repetitive open and closing actuators.

Running axially underneath the longitudinally extending pairs of massage grippers are longitudinally extending tubes of a stationary water supply having air bubbles moving therethrough. The truly unique approach and application of the "dry" hydrotherapy technique used here is that no water pump or external source of water is required. Instead, the water inside the soft vinyl tubes remains stationary or "static", and air from the host air compressor is channeled to and blown through the water, which creates a bubbling, pulsating effect that is very soothing. Although the tubes contain water, no water touches the user but the effect simulates actual hydrotherapy for enhancing the relaxation of a user.

The resistive wire located on the top of these tubes communicate with temperature regulators. The perception of warmth is felt as the bubbling and pulsating action of the dry hydrotherapy passes through the heated resistive wires as a person or an individual limb is lying on them, creating the illusion of the water and air being heated. The hydrotherapy hoses, with the resistive wire on top, are then wrapped with an attractive heat resistant cloth material.

The motive actuators that produce movement of the gripper pairs between the open and closed positions are preferably compressed air compressors.

Furthermore, the massage gripper pairs are connected to the frame by a base support supporting scissors extenders, flexible cables or other open and closing actuators.

The super-soft outer shells of the massage contact pads include a rubber-like elastomeric material having rounded contours for contacting the body of a user. The relatively harder resilient inner liners include rounded contours for providing each outer shell with a contour conforming substantially thereto.

To simulate actual water-applied hydrotherapy or the warm blood-flow induced massage of an actual human masseuse, there is provided longitudinally extending stationary water or other fluid-filled, air inflatable conduits or tubes, which include on exterior surfaces thereof, electric heating elements. These electric heating elements are energized by current supplied thereto by an electrical power source wired through the frame and also within the massage gripper elongated members.

The plurality of air inflatable, stationary liquid filled tubes are disposed within the couch reclining surface, preferably along the same axes as the pairs of massage grippers in the vicinity under the limbs of the user. In other embodiments, they could be located elsewhere, so that they contact any part of the user's body.

These longitudinally extending tubes have two ends, including an air inlet end and an air outlet end. The air inlet end is connected to one or more air bubble supplies disposed within the couch frame and in tubes. These tubes have a layer of temperature controlled resistive wire for heating purposes.

The air bubble supplies produce a forced flowing stream of air bubbles within the stationary water supply of the air inflatable conduit tubes. These tubes respectively have one or more air inlet ports and one or more air escape ports for permitting a continuous flow of bubbles within the tubing. These air bubbles, along with a layer of heat imparting resistive wire, provide a desired relaxation-enhancing environment for the user.

Optionally, the relaxation station further includes a plurality of orbitally spinning rounded-contour shiatzu massage bodies attached to respectively extension stalks, which in turn are attached to and radially project from one or more shiatzu massage hubs, which hubs in turn are attached to the upper end of an upwardly-projecting bent-shaft extension member, which bent-shaft extension member are in turn connected to and project generally upward from a motive source of orbital rotational motion, said orbital rotational motion attached to the couch frame. For example, shiatzu massage bodies may be wooden balls.

A computer system has a computer central processing unit and computer information storage and retrieval unit, which preferably includes an audio signal processor and one or more musical instrument digital interface [MIDI] and loud speakers suitably responsive to the computer system, for presenting a user with a relaxation-inducing audio stream.

The musical instrument digital interface (MIDI) can also avoid complex software for controlling the motion of the massage grippers or the rhythmic flow of the temperature regulated air bubbles simulating water flow by rhythmically controlling the motion of the massage grippers and the pulsation of the air bubbles in the vicinity of the moving massage grippers.

Optionally, the relaxation station has a user controller to regulate the massage gripper temperature and dry hydrotherapy temperature imparted by the resistive wire.

Besides the rhythmically moving massage grippers, the device may optionally have in the couch reclining surface closest to the user one or more orbitally rotatable shiatzu-type segments such as wooden balls on supports, for massaging one or more portions of the user's body, such as, for example, the buttocks.

Another source of massage includes a pair of rotatable eccentrically placed weights having motive actuators and eccentric gear means attached thereto for producing the eccentric rotation of the weights, to further produce non-synchronous vibrations which interfere with each other to produce a third vibratory wave form that contacts the user, preferably in the low back lumbar region.

In a further embodiment, upwardly extending, vertically movable members, such as triangular high hats, push up against the user's body, such as for example, the mid-back thoracic region.

Moreover, all of these moving parts, as well as the air bubble flow, can be controlled rhythmically or in on-off sequences by a musical instrument digital interface (MIDI). The motive actuators are attached to the couch frame. Other optional features include aromatherapy diffusers or fiberoptic lamps.

While the aforementioned preferred relaxation system is provided for the whole body of a user, in a further embodiment there may be provided modular limb-sized massage simulating stations for treating one or more limbs of a user with the plurality of massage gripper pairs within an open sleeve limb accommodating support, into which is inserted a portion of the body, such as a hand, forearm foot, leg or the like. Thus, a simple, interchangeable device can be used on any limb without the need for a whole body relaxation station as in the aforementioned embodiment.

The limb accommodating support has an open frame and a resting surface attached to the frame for accommodating a limb of a user therein. The frame has the plurality of pairs of massage grippers connected to and extending generally upward therefrom. These massage gripper pairs also include elongated members projecting generally upward from the open frame; and they are capable of moving reciprocally between open and closed positions, with the closed position cradling and contacting the limb of a user. Motive actuators to produce movement between the open and closed positions control these massage gripper pairs.

The massage gripper elongated members respectively have attached thereon one or more soft massage contact pads that contact and massage the limb of a user. Each contact pad includes a super-soft outer shell surrounding and attached to a relatively harder resilient inner liner, which, in turn is attached to the elongated gripper members. Like the full body embodiment, in the limb-sized embodiment, the motive actuator for producing movement of the gripper pairs between the open and closed positions is a compressed air supply compressor, and the massage gripper pairs are connected to the limb-accommodating frame by the aforementioned base support supporting scissors linkage extenders or flexible cables, which gripper pairs produce clamping massage motions.

Optionally, these motive actuators connected to the massage grippers to produce open and closing massage motions have an electric motor with reciprocal gearing.

In an alternate embodiment, the grippers may be a single row of hinged digits that open and close toward an opposite fixed member, similar to human hand fingers opening and closing towards a thumb in a fixed, non-moving position.

Preferably, but not mandatory, the limb-sized modular unit further includes a temperature regulator and a dry hydrotherapy source, including a stationary, fluid filled water conduit that may be sealed, with air bubbles flowing therethrough for enhancing the relaxation of a user and to closely simulate water-applied therapy or the warm, blood-flow induced by the warmth of the hands of a human masseuse.

The temperature regulators of the hydrotherapy units have electric heating elements disposed along the longitudinally extending conduits, which electric heating elements are energized by current supplied thereto by an electrical power source wired through the limb-sized support and within the massage gripper elongated members.

This plurality of liquid filled conduits are disposed along the limb resting surface of the support sleeve. These conduits have two ends, including an air inlet end and an air outlet end, wherein the air inlet end is connected to one ore more air bubble supplies which are connected to the limb-sized support sleeve. These air bubbles flow in the tubes which have a layer of temperature controlled resistive wire on an outside surface thereof.

To simulate actual water flow without using much water, the air bubble sources produce a flowing stream of air bubbles within the tubes, which respectively have an air inlet port and an air escape port to permit a continuous flow of air bubbles within the tubing.

The layer of resistive wire provides a desired relaxation-enhancing user-controlled temperature to the limb being treated.

Optionally, the limb-sized open support sleeve includes a computer system with a computer central processing unit and a computer information storage and retrieval system. The computer system includes optionally at least one musical instrument digital interface [MIDI] suitably responsive to the computer system, to rhythmically control the pulsation of the gripper pairs or the pulsation of the air bubbles.

Optionally, a user controller for regulating gripper temperature and dry hydrotherapy temperature is provided.

While it is preferable to have both massage grippers and dry hydrotherapy components in a limb-sized modular support sleeve, in situations where the massage is not needed, the limb treating support sleeve that accommodates the limb of a user can have attached thereon only the dry hydrotherapy device, for contacting the body of a user with dry heat which simulates the application of warm water flow, as in Jacuzzi-type jets.

As noted previously in the discussion of the limb-only embodiment with both massage grippers simulating finger massage and with dry hydrotherapy simulating warm water applied to the limb, in this further embodiment there is also included temperature regulators and dry hydrotherapy supplies to treat a limb of the user. In this case, the temperature regulators also have electric heating elements disposed along the longitudinally extending fluid filled conduits, which electric heating elements are energized by current supplied thereto by an electrical power source wired through the limb-sized support sleeve member. Similar to the first, whole body embodiment, in this limb-only embodiment, the conduit tubes have two ends, including an air inlet end and an air outlet end, and the air inlet ends of each conduit tube are connected to the air bubble supply which is connected to the limb-sized open support sleeve. The air bubble supply has a layer of heat imparting resistive wire for imparting heat to the user.

These tubes respectively have an air inlet port and an air escape port to permit a continuous flow of air bubbles within the tubing; to provide a desired relaxation-enhancing user-controlled temperature which simulates water-based hydrotherapy.

Moreover, this hydrotherapy-only limb-sized open support sleeve can optionally have pulsations of air bubbles which are controlled by a computer system having a computer central processing unit means and a computer information storage and retrieval unit, with a musical instrument digital interface [MIDI] for regulating the rhythmic pulsation of the flow of the air bubbles simulating the water-based hydrotherapy.

With respect to the details of the present invention, the key areas the relaxation station uses for stress relief are: Concerning the aforementioned massage grippers, the pneumatically (or otherwise—hydraulic, electric, electromechanical, etc.) controlled and heated robotic-like grippers act as "body fingers" to open and close, applying pressure to multiple areas of the body simultaneously. The computer controlled MIDI software-sequencing program controls the opening and closing of the grippers, using MIDI-to-control voltage converters. The pneumatically (or otherwise—hydraulic, electric, electromechanical, etc.) controlled leg truss mechanism is switch controlled, and retractable to allow the user to climb aboard the relaxation station, and then rises up again to position for massaging the legs.

A pivoting half-round chrome metal mount (which holds the computer screen, computer keyboard, speakers for nature sounds audio system, aromatherapy diffuser, ionizers, and the six fiberoptic lamps) also swings out of the way for climbing aboard the relaxation station, and then swings back (manually) again into position (and locks) for easy viewing and reach while laying down.

A spring-loaded cylinder assembly is provided for the feet, to adjust for varying leg lengths. The right foot cylinder assembly also snaps and locks into place, allowing more room while climbing aboard the relaxation station. A second push with the foot returns the cylinder assembly back into its normal operating position. Three of the cylinders are incorporated with wooden "hi-hat" (triangular shaped and pointed at the top like a spin top) blocks used for back massaging, and are mounted directly onto the rod clevis of the pneumatic cylinder shaft. The dry, heated hydrotherapy is preferably provided. Dual eccentric motors provide for "wave" massage.

Also, preferably there are two full-range sound systems. The first is for playback of nature sounds, and the second for playback of soothing music. A digital delay unit is used, patching the output of the first sound system into the input of the second, creating a "surround-sound" effect for the nature sounds. Other optional features include an aromatherapy diffuser, a pair of negative ionizers, and a plurality, such as six fiberoptic lamps, and a 3D-imaging program synchronized to the soothing music and displayed on the computer screen for the user to view. Optionally there is also provided a modem, with a telephone, and a digital camera connected to the computer for use with a user-selected web site on the Internet. Magnet therapy may also use a pair of magnetic footpads, and a cup holder with a cup may be provided for ingestion of teas.

To achieve these stress-relieving results, the following details of the system are disclosed:

The relaxation station provides a plurality of, such as 52, air-driven robotic "fingers" resulting in a truly "digital" massage.

The present embodiment utilizes a plurality of, such as 34, prelubed stainless steel, double-acting pneumatic cylinders. They have a ¾ bore, are nose-mounted using rod clevis mounts, without pins, on selected piston rods, do not use magnets or bumpers, and are "Buna N" packed.

The stroke length of a majority of the cylinders, such as 26 cylinders is 1¼ inches, and the stroke length of the remaining 8 cylinders is 6 inches. The 6-inch stroke cylinders have a separate and unique purpose—to be described shortly. A pair of modified "scissors folding" reach extenders which behave like robotic "grippers", are mounted on each rod.clevis of the 1¼ inch stroke cylinders using ⅛ inch threaded stock, which is lubricated with white grease to reduce friction.

Alternatively, the reach extenders can be substituted with flexible cables connected to respective robotic finger grippers, wherein the flexible cables are mounted on the respective rod clevises.

The metal extensions of each reach extender are covered with two types of rubber.

The first and bottom layer of rubber is a hard compressed, elastomeric, such as rubber, much like that of a "super-ball" that measures preferably about 13/32 inches in diameter, and is essentially a circular ball cut in half which creates two semi-spherical halves. Each semi-spherical half is mounted on the reach extender arm "flatside" down. This creates a rounded "bump" protruding off the reach extender arm. These "bumps" simulate the bumps and ridges of the knuckles on a human hand. There are a total of five of these "bumps" on each half of the reach extender arms, which is more than a human hand would have, yielding a total of ten half-rounded "knuckles" per reach extender.

The second and outer layer of rubber is a special "super soft" rubber ball that measures preferably 38 mm in diameter. Each ball is left intact in its rounded form. A fine hole is punched through each of these balls so that they may stretched and slid over each of the reach extender arms, completely covering the compressed rubber semi-spherical "knuckles". This super soft rubber is used to simulate the muscles and skin consistency, elasticity and pliability of the human hand.

To create the heat and warmth of the human hand, thermostatically controlled resistive wire, protected with an elastomeric or other rubber coating, is wrapped and weaved around the outside of the "super soft" layer of rubber and then continues on to each of the other reach extenders in the group of user controlled "heat zones". There are four independent heat zones. The first zone is for the left side of the body, which includes the legs, arms, and shoulders. The second zone is for the right side of the body, which also includes the legs, arms, and shoulders. The third zone is for just the feet—both left and right, and the fourth zone is for heating the hydrotherapy water lines. More on the hydrotherapy portion of the relaxation station is described later herein.

Each completed reach extender assembly is then covered with a flame-retardant material for cosmetic purposes.

Each cylinder assembly for the feet is spring loaded to adjust for varying leg lengths. The right foot cylinder assembly also snaps and locks into place, allowing more room while climbing aboard the relaxation station. A second push with the foot returns the cylinder assembly back into its normal operating position.

Three of the twenty-six 1 ¼ inch stroke cylinders are used for back massaging. These cylinders do not use the "gripper" mechanism but instead have a pair of wooden "hi-hat" blocks, which are triangular shaped and pointed at the top like a spin top, and which are mounted on "L" brackets. The "L" brackets are then bolted onto ¼ inch threaded stock, which in turn is attached to the rod clevis of the pneumatic cylinder shaft. As air is applied to the cylinder, the triangular shaped blocks raise and lower in an up and down motion, pushing on key areas of the back of the person lying on them. The effect is similar to someone using their thumbs to dig in and massage these areas of the back.

There are preferably eight 6 inch stroke pneumatic cylinders that are used to raise and lower the custom designed leg truss mechanism, which also has the motorized "moving ball" massage assembly mounted, thereon. When an individual wishes to "climb on-board" the relaxation station, a semi-circular chrome-metal bar which contains the overhead computer screen/front speakers/ionizer assembly is swung out of the way. A power control switch is used to lower the leg truss, upon which the pneumatic "grippers" for the legs are mounted, down and also out of the way.

Once the individual is comfortably seated, the power control switch is used again to apply air to the cylinders so that the entire leg truss rises up to the proper and final position under the legs. The semi-circular computer screen/front speakers/ionizer assembly is also pivoted and swung back into its ergonomically useful position.

The source of air pressure comes preferably from a 3.5 horsepower, 11 gallon compressor with built-in regulator, which supplies a maximum air pressure of 125 psi, 8.1 @40 psi SCFM, and 6.1 @90 psi SCFM. The regulator is set to provide an air pressure of approximately 90-psi.

An air fitting male connector from the compressor connects a length of ¼" OD plastic tubing to three union "T" connectors, which then split the airflow into four "10 station" manifolds. Each manifold has two ⅛-inch mufflers, making a total of 8 to quiet or mute the sound of the air exhaust.

There are preferably a total of forty stations available (4×10) and only 34 of them are used for the cylinders. Four of the remaining six stations are plugged with caps to prevent air loss and the remaining two stations are used to feed the simulated hydrotherapy water tubes. Each individual station on the manifolds then outputs to a 5⁄32-inch air hose, which is then connected to each of the pneumatic cylinders.

To switch and reverse the direction of the airflow, which opens and closes the modified reach extenders, basemounted 120 VAC pneumatic valves are employed. The valves measure 15 mm wide with a flow of 0.25 Cv. They are the single solenoid, standard solenoid operator type, with a port size of ⅛ inch to accommodate the manifold ports.

In-line flow control valves are used to regulate the rate of airflow both to the cylinders and from the returns (i.e. the output) of the cylinders. This action affects how quickly the modified reach extenders will close and clamp down on a given body part, such as a leg, arm, neck, etc. and open-up or release.

The order or sequence that the pneumatically controlled reach extenders open and close to grip and release is controlled by the use of the aforementioned musical instrument digital interface (MIDI) software sequencer program which is controlled by a Pentium class or better "host" computer. This computer should have at least 32 megabytes of RAM, and 1 gigabyte or more of hard drive space. Each set of pneumatic grippers is assigned a musical note that can be recorded into and then played back from the musical sequencer. Therefore, it is possible to "program" any order or sequence of notes to be played back from the computer—directly affecting the sequential opening and closing of the grippers. The MIDI-to-CV (control voltage) converters are used to change the binary serial MIDI output signal(s) into voltage information that directly affects the valves that control the switching action of the air flow to the pneumatic cylinders.

The preferred MIDI-to-control voltage interface is the LIGHT MASTER by Topaz Industries. In this MIDI, there are two MIDI ports, four power outlets, one power inlet, a fuse access hole and a 10 switch Dip.

Connection is by hooking a MIDI plug from the computer's MIDI out, into the MIDI-to-control voltage "MIDI in" port, plugging the 120 VAC pneumatic valves in, setting the MIDI address on the Dip switches and plugging the power cord into a 15-amp power outlet. For daisy chaining additional MIDI devices, connection is made with another MIDI cable to the MIDI OUT of the MIDI-to-CV converter to the MIDI IN of the next device in the chain. In this case the next devices are additional MIDI-to-control voltage devices. The 120 VAC pneumatic valves are connected to the power plugs of the MIDI-to-CV power outlets. The power rating is 600 watts (5 amps) per outlet and a maximum of 1800 watts (15 amps).

There is a configuration switch module (DIP switch) located at one end of the Topaz LIGHT MASTER MIDI interface. The switch settings are as follows:

A first switch 1 is for the Baud rate. "Up" is the MIDI Baud rate (31250), "Down" is 9600. This is included if becomes necessary to run the system off the serial port of the PC compatible computer since most IBM compatibles will not run the standard MIDI baud rate off their COM ports. The on-board computer of the relaxation station is set to the standard MIDI baud rate of 31250 bps (Bits Per Second).

The second through sixth switches are Bank number switches. These switches represent binary numbers, thus the right most sixth switch is the least significant bit. Value of the switches can be 0–31.

The seventh through tenth switches are MIDI channel switches. These switches represent binary numbers, thus the right most tenth switch is the least significant bit. There are tables for switch settings as well. In addition, dipswitch settings are read at "power up" only.

The MIDI-to-control voltage device can be controlled via 'Note On' mode or the 'Program Change' mode.

The relaxation station utilizes a new design in the aforementioned hydrotherapy, for limbs such as all or part of the arms and legs, which creates a Jacuzzi-like bubbling waterflow simulating action, but leaves the user totally dry.

This unique "dry" hydrotherapy uses two 1 ½ inch diameter soft vinyl hose lines, such as, for example the same hose used for swimming pool back-washing purposes, which run under the left and right legs and arms, and terminate in the air, raised above and behind the head. Each vinyl hydro line is approximately 9 feet in length, and, is pre-filled with approximately 12 ounces of tap water. A couple of drops of chlorine and permanent algaecide are added to the water for sanitary purposes.

The truly unique approach and application of the "dry" hydrotherapy technique used here is that no water pump or external source of water is required. Instead, the water inside the soft vinyl tubes remains stationary or "static", and air from the host air compressor is channeled to and blown through the water, using ¼ inch outer diameter O.D.×0.170 linear diameter L.D. vinyl air tubing, which creates a bubbling, pulsating effect that is very soothing. The air tubes that lay inside the water tubes have their ends plugged and have a series of small holes drilled along the sides of them in order to allow the air pressure to escape. Only about 20–24 inches or so of air tubing which is actually inside the water tubes is necessary.

This is because the weight and pressure of the person lying on top of the tubes forces the air (and water) to be squeezed and spread out to rest of the system. The actual bubbling and pulsating effect is created as the air is forced through the water and is preferably controlled by the rhythms of the musical instrument digital interface (MIDI). The airflow is then allowed to escape through the exhaust valves at the end of the hydrotherapy lines, which are located up by the head. The ends of the hydrotherapy hoses, located by the user's head are, for gravity reasons, raised up higher than the user's head, so that water is not allowed to run or pour out of the system.

The amount of air pressure is regulated and controlled by adjustable needle valves located on one of the manifolds, preferably a ten-station air manifold. The exhaust valves at the other end of the soft vinyl tubes, by the head, are used to regulate the amount of backpressure in the system. These valves are set to create just enough backpressure so that the tubes can partially inflate as air is blown into and through the water. The partially inflated tubes provide a soft air cushion under the arms and legs, and it is this air cushion that bubbles and pulsates, as a direct result of the bubbling water, which creates the hydrotherapy effect.

Without the backpressure valves, there would be no resistance and the hydro tubes would lay flat and the effect would be minimal if noticeable at all. If the backpressure valves are closed-off too much, the tubes might over-inflate, and thus no pulsating action would be felt. Having the correct amount of backpressure in the hydro system is one of the keys to how the dry hydrotherapy system creates its wonderfully soothing effect. So it is the action of the air being blown through the water, and not the force of a pump circulating the water, which creates this truly unique effect.

To further enhance the soothing effect of the dry hydrotherapy, adjustable heat can be applied, using coated, protected resistive wire which runs completely along the outside on the top of the soft vinyl hydro tubes. There are two reasons for this.

The first is because if the resistive wire ran on the inside of the tubes through the water, an electrical hazard could be present—even if using low voltages. In addition, the water would tend to act as a heat sink, cooling off the wire. Therefore a much, much larger amount of voltage would be necessary in an attempt to create heat, and this further adds to the potential electrical hazards, not to mention the deterioration of the wire itself from excessive voltage, and of the corrosive properties of the chlorinated water. If a heating element, metal or otherwise, of some kind were used to heat the water instead of the coated resistive wire, the amount of heat necessary to heat the water to a suitable temperature would melt the soft vinyl tubing, creating still another hazard.

The second, and perhaps most important reason for running the heating lines on the top of the outside of the hydro tubes is because it is actually not even necessary to heat the water at all. The perception of warmth is felt as the bubbling and pulsating action of the dry hydrotherapy passes through the heated resistive wires as a person or an individual limb is lying on them, creating the illusion of the water and air being heated. The hydrotherapy hoses, with the resistive wire on top, are then wrapped with an attractive heat resistant cloth material.

Mounted on the leg truss mechanism of the full body relaxation station is the motorized "massage ball" mechanism, designed to service the buttocks area. This mechanism is essentially a modified shiatzu unit where the hard rubber balls at the end of the two slightly bent metal rotating shafts have been removed and replaced with two multi-shaft wooden massage balls. The wooden massage balls sit on the "bent" metal shafts and are allowed to freely spin on the shafts. The metal shafts are bent at an approximate angle of 15 degrees. As the bent metal shafts rotate, the wooden massage balls also rotate, but at a different rate than that of the metal shafts, because the metal shafts are allowed to spin freely inside the wooden massage balls. The metal shafts are lubricated with white grease to reduce friction. There are four metal "bumpers" which act as "stops" to prevent the wooden balls from rotating into each other and becoming jammed. As the metal shafts rotate, the wooden massage balls also rotate, but also rise up and down a bit (because of the angle created by the bent shafts) creating a mild but soothing kneading effect.

The only other motors used in the relaxation station are two small 110–120 V A.C. motors, located and placed under the lumbar lower back region of the person lying down. These motors are encased in plastic, and are placed directly next to one another, in very close proximity. The reason for this is because the speed of the two spinning motors are purposely not synchronized with each other, even though they are "supposed" to be spinning at the speed.

At the end of the shaft of each motor, a small round weight is eccentrically (off-center) mounted so as to throw the spinning of the shafts slightly "off balance" intentionally causing soft vibration.

As the two motors spin freely and independently of one another, the rate of their speeds will tend to drift in and out of synchronization, thus creating in effect a third wave of pulse that is a mathematical division of the rate of the speeds of the two motors.

To further increase this effect and to make the effect even further pronounced, a variable speed resistor (or rheostat, etc.) is used to drastically reduce the speed of the motors. If the motor spins at anywhere from 2000 rpm 3500 rpm for example, the speed would be reduced to, let's say, 80 rpm–500 rpm. At this lower speed the effect of the third "wave" is felt as a gentle pulse in combination with the vibrations of the original speeds of the motors, and the "non-static" effect of this asynchronous combined slow speed spinning action is really quite soothing.

An optional aromatherapy diffuser surrounds the user with pleasing lavender and other relaxing aromas, which set the user's mind at ease. The present embodiment uses a 110–120 V A.C. motor with fan blade assembly mounted in a plastic case, which blows air up to and around a pad, which is pre-soaked with an aromatherapy "essential oil". The pleasing aroma of the oil is picked up as the fan blows air past the pad and is distributed evenly around the room.

Two ionizers charge the surrounding air with negative ions to create a "just after the rainstorm" freshness in the air. These negative ionizers are designed to generate copious streams of negative ions, which combine with dirt and dust particles in the air like magnets. The airborne particles and odors are removed from the air by the process of electrostatic precipitation. The negatively charged particles then become attached to positively charged surfaces such as floors and walls. The ionizers effectively eliminate airborne bacteria and dispel unpleasant smells (tobacco, cooking, pet odors, etc.). Each ionizer runs on 12 VDC @60hz, uses 5 watts of power, and is rated at 200 milliamps.

Two full-range sound systems with sub-woofers and electronic surround-sound create an ambience that virtually "sends" the user to another simulated place. The first sound system is used to reproduce nature sounds (tropical birds, crickets, rain, etc.). The second sound system plays soothing and calming music selections used to create the proper "atmosphere", and when blended with the calming nature sounds, creates a listening experience that is totally tranquil. A digital delay system is used on the first audio system and is returned back through the second audio system, creating a wonderful "surround-sound" effect on the nature sounds. This effect really makes the listener-user dissolve into the mood created by this total sonic experience, which of course enhances and adds to the total overall relaxation experience.

Optionally, visual relaxation happens by gazing at the six fiber-optic lamps, each of which has thousands of hair-thin fiber-optic strands measuring approximately 10 inches in length. They extend up and out and then drape over like a beautiful willow tree. Grouped tightly together in the middle section at the base and lit by a 15 watt 120 VAC light bulb from underneath, a motor with a multi-colored template on top of the light source slowly rotates through the color spectrum creating an almost "aurora borealis" like experience.

The computer's overhead video screen is also used to create visually relaxing effects. By use of various 3-dimensional geometric rendering programs such as KINEMORPHIC 3D which use X, Y, and Z axis algorithms, and others, it is possible to have beautiful on-screen images, including fractals, float and swirl around the computer screen—all synchronized to the soothing music provided by the music portion of the relaxation station.

The host computer has a built-in modem (currently 28.8K, 56K or faster is preferred) which is used for connection to the Internet. By logging on to a pre-selected relaxation station web site; further visual relaxation can be achieved by viewing animated movie loops of sunsets, waterfalls, mountains, forests, beaches, and more.

A "live" relaxation station spokesperson(s) (male and/or female) is also available at the web site, for talking through various relaxation affirmations and breathing exercises. Through means of the built-in camera on the relaxation station it is possible to have live 2-way tele-video conferencing with the spokesperson and/or other individuals who are logged onto the web site. A telephone is included on the relaxation station for convenience and to share the wonderful stress-relieving experiences with friends.

Finally, magnetic acupuncture footpads are attached to where the feet rest, intending to reduce muscular aches and pains, headaches, and fatigue. There are preferably seven strategically placed magnets in each footpad. The insertion of the magnetic capsules are situated as to become pressure points operating as in acupuncture on the plantar regions of the feet, stimulating blood circulation.

The only sense (of the five human senses) that isn't directly addressed is the sense of "taste". It was determined that it was not very practical to have a tube or some other "feeder" mechanism aimed at or even placed in the mouth of the person relaxing.

Therefore, a cup holder with cup is mounted on the left side of the relaxation station where an individual may sip their beverage of choice. This indeed opens up the possibility of creating a line of soothing herbal relaxation station teas, ranging anywhere from chamomile to passionflower.

The current embodiment uses a STANLEY LIGHTMAKER wireless 110–120 VAC transmitter/receiver power control system (merely for convenience purposes) to control various components of the relaxation station. This system uses the X10communications "language" which allows compatible products to talk to each other, using a power line carrier via the existing 110 VAC electrical wiring in the home. Up to 256 different addresses are available. If more than one device is required to respond to the same signal, simply setting them to the same addresses accomplishes this. All X10 compatible products can be freely mixed and matched. STANLEY products can be used together with Leviton's X10 POWERHOU.S.E, etc. Each outlet is 120 VAC, 15 amps, and rated at 500W.

The following components of the relaxation station are controlled in this manner by this power control system:

1. Leg truss up/down power;
2. Audio system power;
3. Fiberoptic lamps' power;
4. Aromatherapy diffuser power;
5. Negative ionizers' power;
6. Heat thermostat power for the left and right side pneumatic grippers for the legs and arms;
7. Heat thermostat power for the pneumatic grippers for the feet;
8. Hydrotherapy heat thermostat power (The power and speed controls for the dual eccentric back massage motors are independently controlled and have their own set of switches.)

Moreover, in the whole-body relaxation embodiment, there are a total of sixteen separate massage zones that are ssigned to MIDI-to-control voltage converters. They are:

1. Left Foot
2. Right Foot
3. Left Calf
4. Right Calf
5. Left Hamstring
6. Right Ham-String
7. Buttocks
8. Lower Back
9. Upper Back
10. Neck
11. Left Shoulder
12. Right Shoulder
13. Left Upper Arm
14. Right Upper Arm
15. Left Lower Arm
16. Right Lower Arm As noted before, in the optional limb-only embodiment, respective massage zones and dry hydrotherapy zones are similarly controlled. However, because only the weight of a single limb is supported, as opposed to the whole body of the user in the relaxation station embodiment, since the compressor only has to supply a low amount of low pressure air to bubble through the dry hydrotherapy hose, small low pressure compressors will suffice.

BRIEF DESCRIPTION OF THE DRAWINGS

The present invention can best be understood in conjunction with the accompanying drawings, in which.

DETAILED DESCRIPTION OF THE PREFERRED EMBODIMENTS

Figure 1:
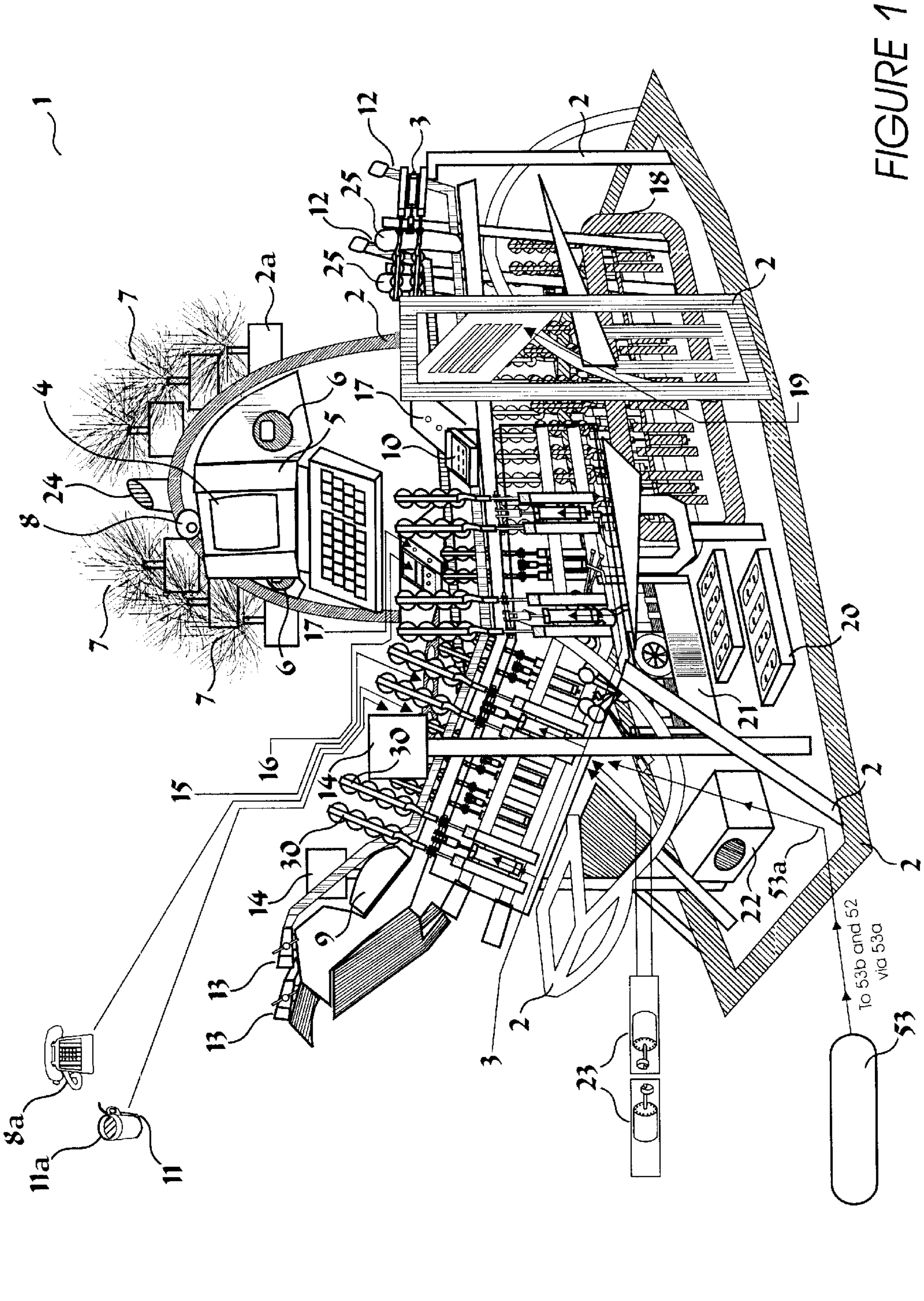
FIG. 1 is a perspective view of the whole body relaxation station embodiment of the present invention.

FIG. 1 shows an abstract view of the relaxation station 1. In the preferred embodiment, several of the powered subsystems involving actuators are pneumatically driven by a remotely located air compressor with a storage tank 53. A complex tubular frame structure 2 supports and provides attachment for the various components. Pneumatic cylinder and gripper assemblies 3 are distributed in different locations.

An optional video display with keyboard 4 provides visual stimulation as do the fiberoptic lamps 7.

Speakers for an optional nature sound system 5, an aromatherapy diffuser 24, and two negative ionizers 6 straddle display 4.

An optional digital camera 8 aimed at the user's head provides a port for visual two-way communications, and a modem with telephone 8*a* is also provided. Optional cup holder 11 with cup 11*a* is provided for ingestion of beverages. A pillow 9 is provided for the head.

A power control center 10 and one or more heat control modules 17 distribute heat to the subsystems.

Speakers for the optional music system 14, a sub-woofer 22, a second sub-woofer for nature sounds 19, and digital delay unit 15 round out the audio subsystem.

A Pentium-class or greater computer 16 executes musical instrument digital interface (MIDI) software to control a variety of solenoid valves and power relays through appropriate interface modules, such as the MIDI-to-control-voltage converters 20.

Feet/ankle gripper pairs 30, magnetic foot pads 25 and leg truss assembly 18 service the lower limb needs.

An optional modified Shiatzu unit 21 massages the buttocks area. Dual motors with eccentric weights 23 provide a wave massage for the lumbar lower back of the user.

Dual hydrotherapy hoses 12 terminating in adjustable exhaust jets 13 provide a dry hydrotherapy subsystem with heat.

Figures 2, 3:
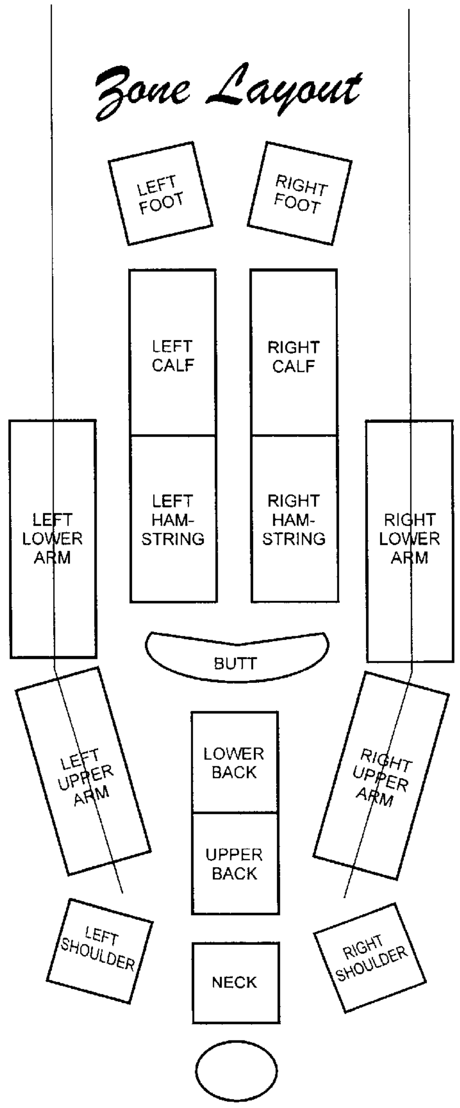
FIG. 2 is a list of power control relay functions thereof.
FIG. 3 is a top plan view zone layout of the relaxation station as in FIG. 1.

Power control relays are used to provide a means to control power to a variety of subsystems. The eight relays are listed with their function in the table of FIG. 2. The relaxation station 1 is divided into several zones by the areas of the user's body that are relaxed by the system; these zones are shown in FIG. 3, which is a top plan view.

Figure 4:
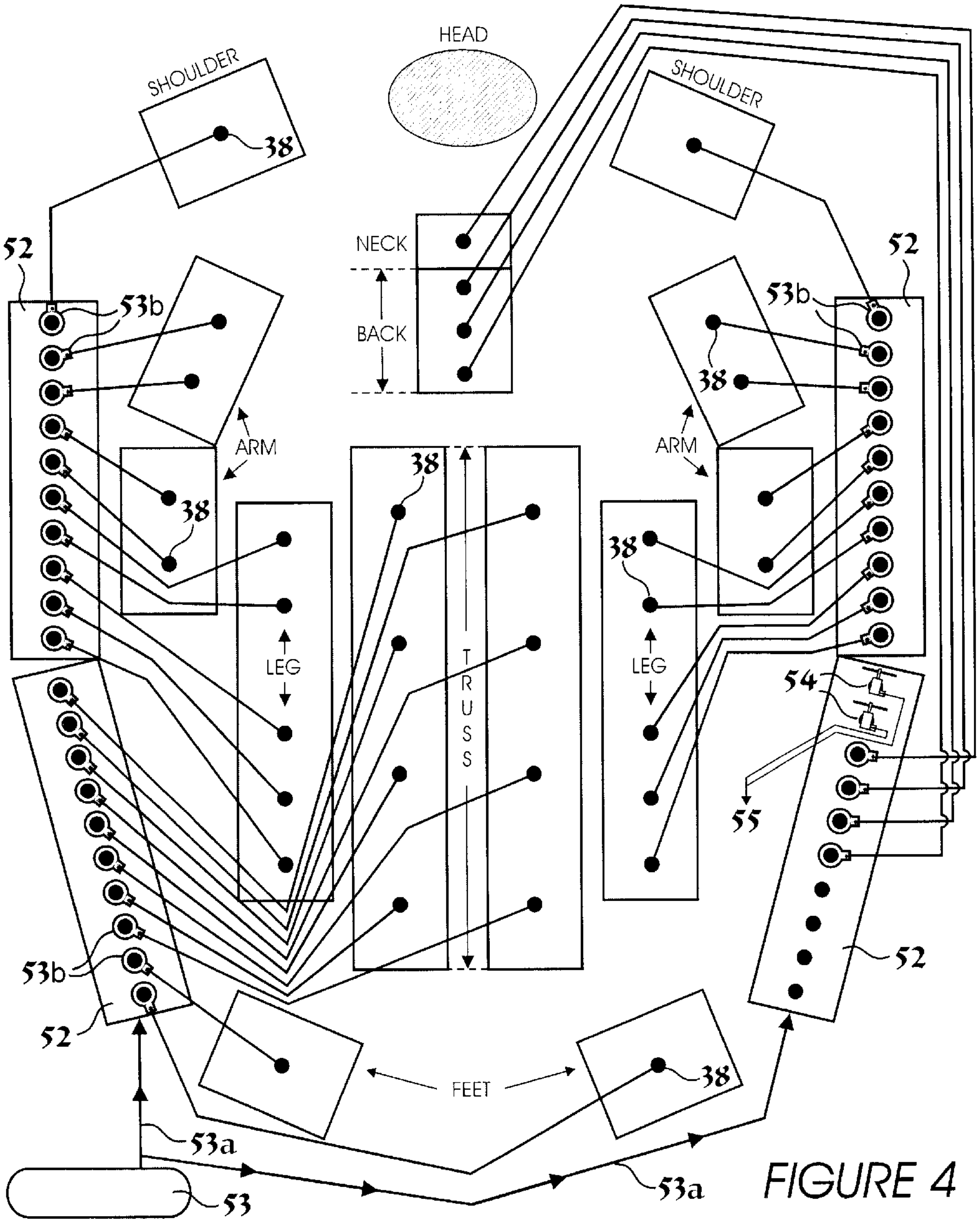
FIG. 4 is a pneumatic schematic diagram showing plumbing of manifolds to various devices in the relaxation station embodiment of FIG. 1.

FIG. 4 is a pneumatic plumbing schematic showing compressed air source 53 and compressed air line 53*a* leading to manifolds 52 having the compressed air lines (each pair is shown as one line) leading to cylinders 38. Manifolds 52 also have flow controls 53*b* servicing each zone, as connected to the manifolds 52, such as four 10-station manifolds.

FIG. 4 also shows the compressed air flow producing movement of massage gripper pairs 30 between open and closed positions by compressed air source 53, such as an air compressor.

Figure 8:
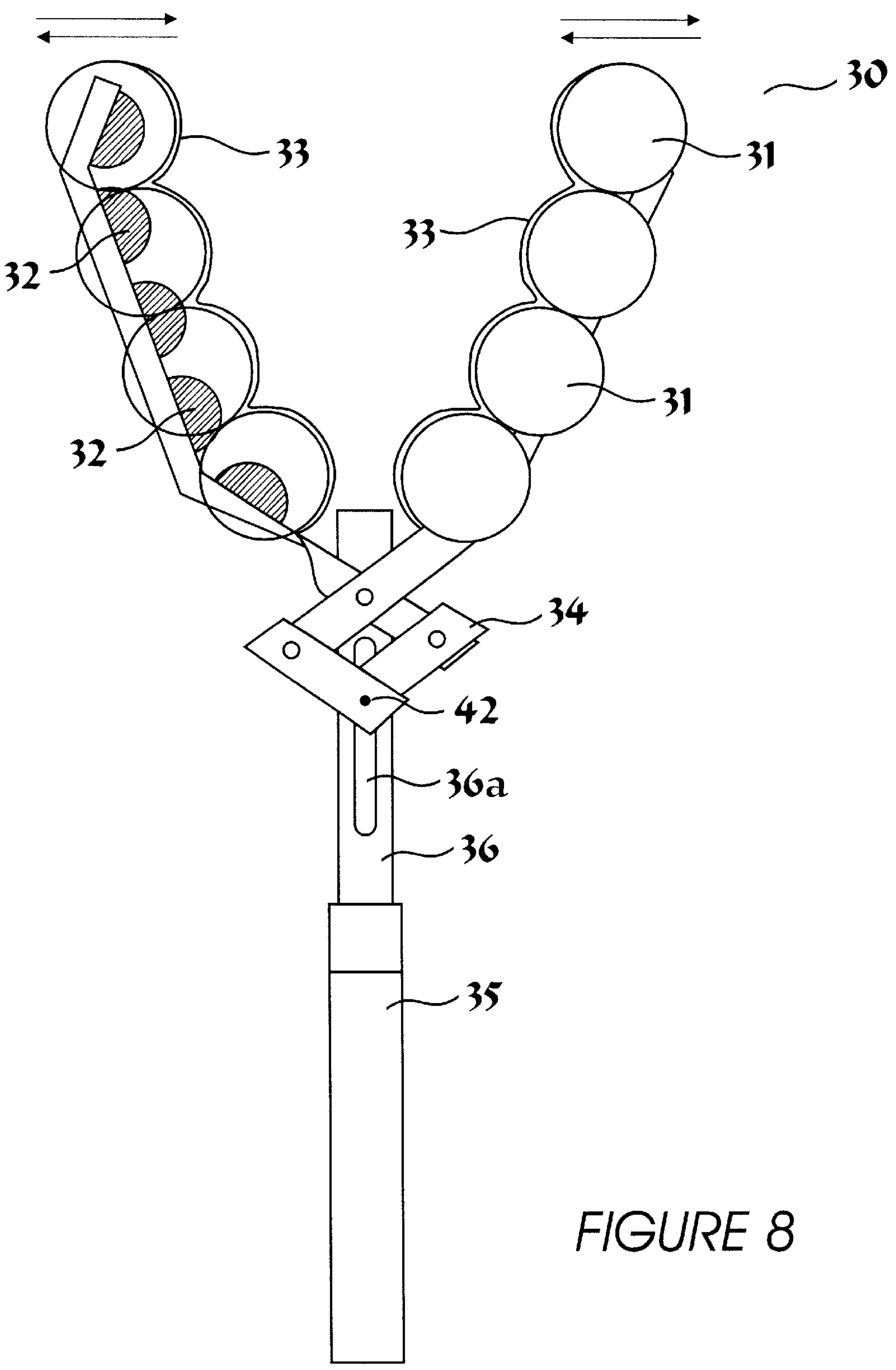
FIG. 8 is an end view in partial cross section of a cylinder actuated scissors extender-controlled massage gripper pair thereof.

As shown in FIG. 8, massage gripper pairs 30 connect to frame structure 2 by base support 35 supporting scissors linkage extenders 34 for producing clamping massage motions.

Compressed air source 53 provides the pressurized source of air producing the clamping massage motions of gripper pairs 30. The clamping massage motions of gripper pairs 30 are further modified by respective in-line flow control valves 53*b* regulating a predetermined rate of air flow of the pressurized-air, wherein the predetermined rate of pressurized air flow controls the rate of the opening and closing of gripper pairs 30.

Figure 5:
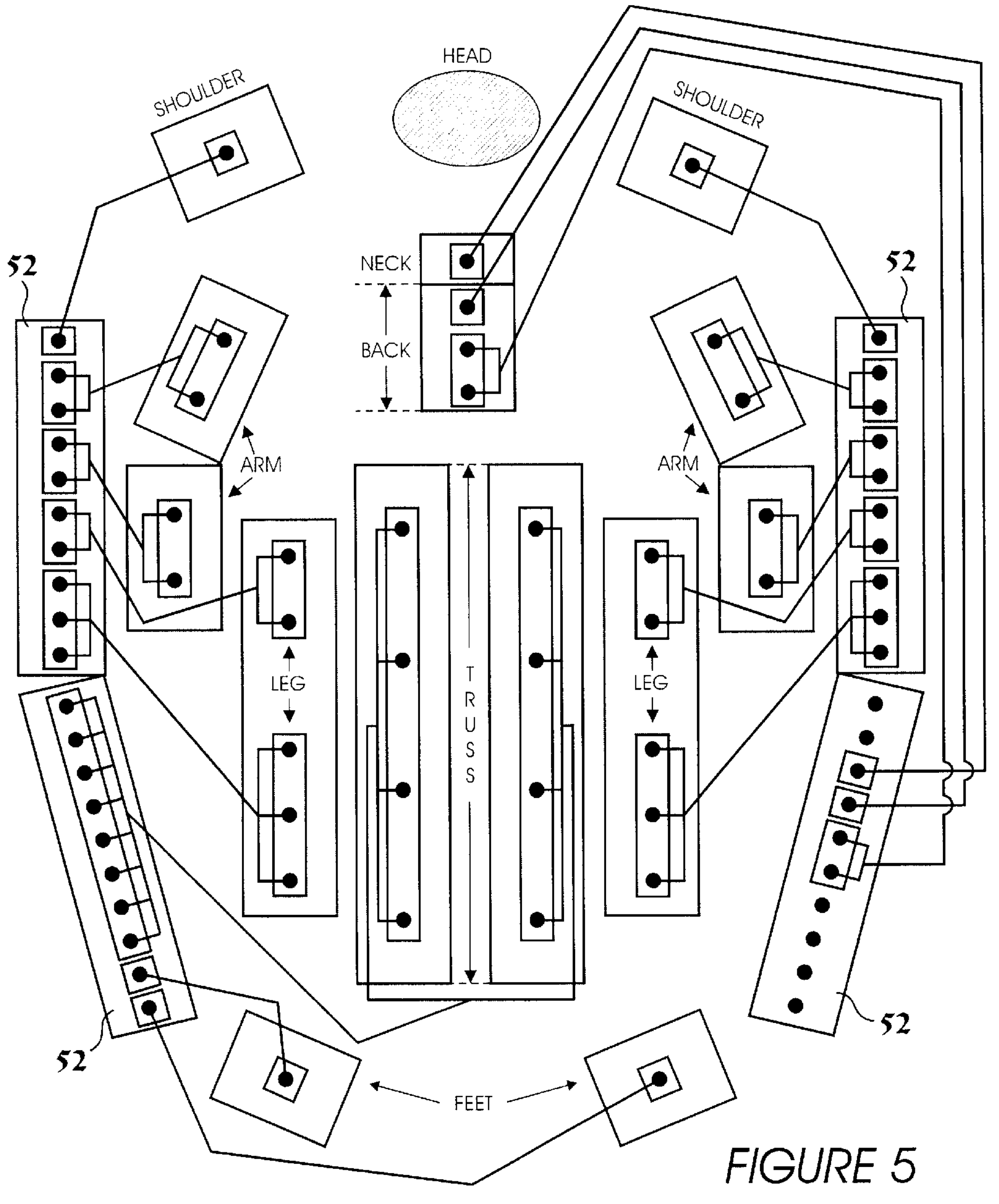
FIG. 5 is an electrical schematic diagram of the solenoid valve wiring thereof.

FIG. 5 is a similar wiring schematic showing the solenoid valves controlling each of the pneumatic lines of FIG. 4. FIG. 5 also shows that all valve switching is controlled by MIDI from host computer 16, except for leg truss assembly 18, which is controlled by a separate switch relay of power control center 10, as also shown in FIG. 2. However, in an alternate embodiment, leg truss assembly 18 could also be controlled by MIDI from host computer 18.

Therefore, the present invention also discloses the use of MIDI to control mechanical moving parts, such as actuators, such as opening and closing of grippers 30 by power sources, such as valve switching connected to the manifolds 52 controlling the direction of the air flow from compressed air source 53.

Figure 6:
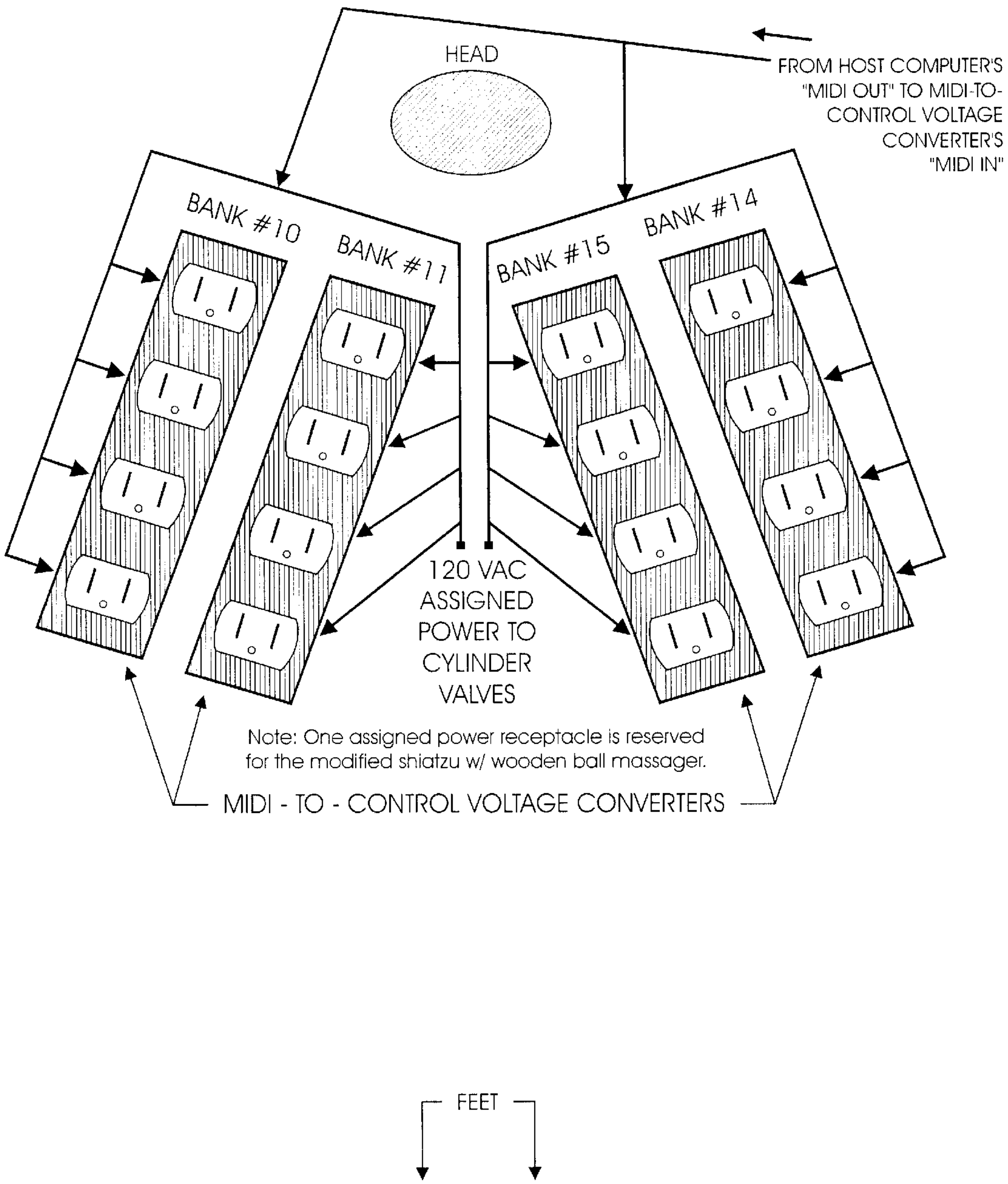
FIG. 6 is an electrical wiring diagram of the musical instrument digital interface (MIDI) to control voltage converters thereof.

FIG. 6 shows the MIDI-to-control voltage converters as laid out on the base of the relaxation station 1; these interface to the solenoid valves of FIG. 5 as well as the Shiatzu unit 21.

Figure 7:
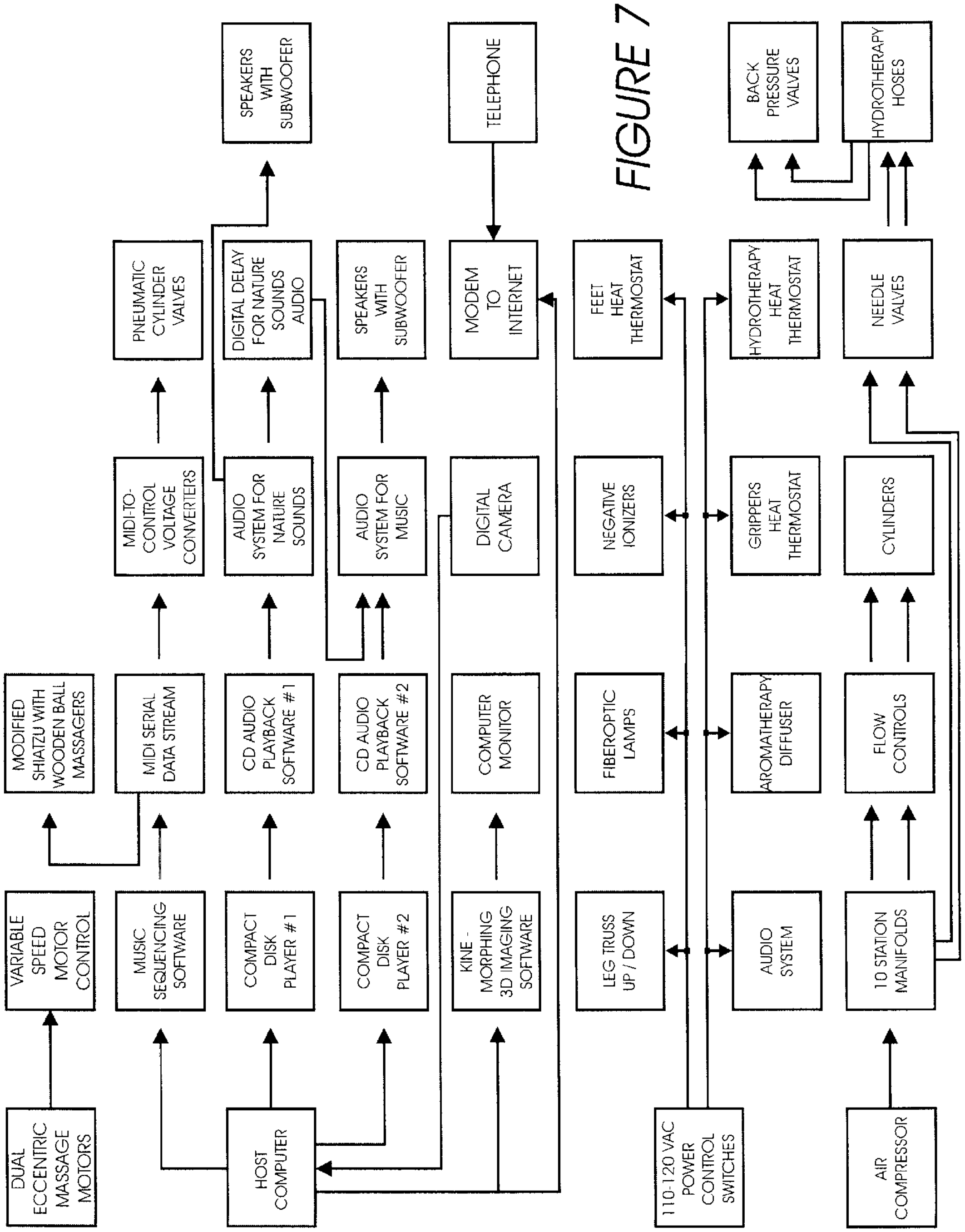
FIG. 7 is a functional block diagram of the whole body relaxation station embodiment of FIG. 1.
Figure 9:
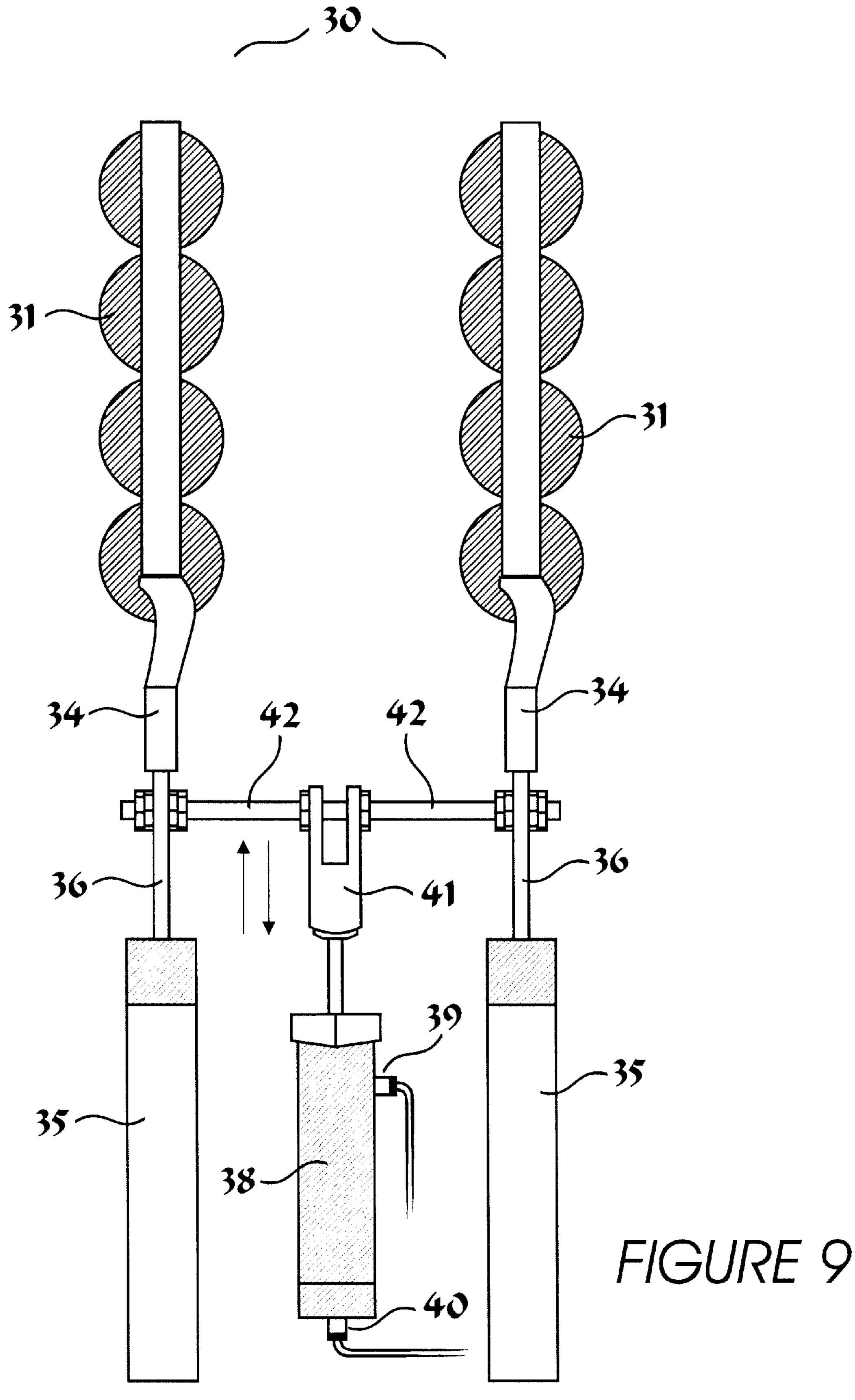
FIG. 9 is a side elevational view of the cylinder actuated gripper pair as in FIG. 8.

The functional block diagram of FIG. 7 shows the interaction of control signals as well as both electrical and pneumatic power flow. The host computer through MIDI music sequencing software controls pneumatic cylinder solenoid valves and the Shiatzu massagers. The computer also controls two CD players, the kine-morphing three dimensional 3D imaging software, and displays images from the digital camera onto the video monitor. The 110–120 VAC power control switches interact with the eight subsystems shown. The air compressor provides pneumatic power for all of the cylinders and also provides compressed air for bubbling through the FIG. 8 and FIG. 9 also show an end view and a side elevational view respectively of a massage gripper 30 with soft rubber balls 31 lining each of the jaws. Hard half-round rubber ball sections 32 within each of the soft rubber, balls provide the proper "feel" for the deep massage action, as also shown in FIG. 8. Scissors linkages 34 interact with connecting rod 42 sliding within the slot 36*a* in upper It g support 36 to provide the gripping action, as also shown in FIG. 8. The lower member 35 is the base support for upper support 36*a*, as shown in FIGS. 8 and 9. Optional resistive heat wire 33 may be provided for heating grippers 30, as shown in FIG. 8.

Figure 8A:
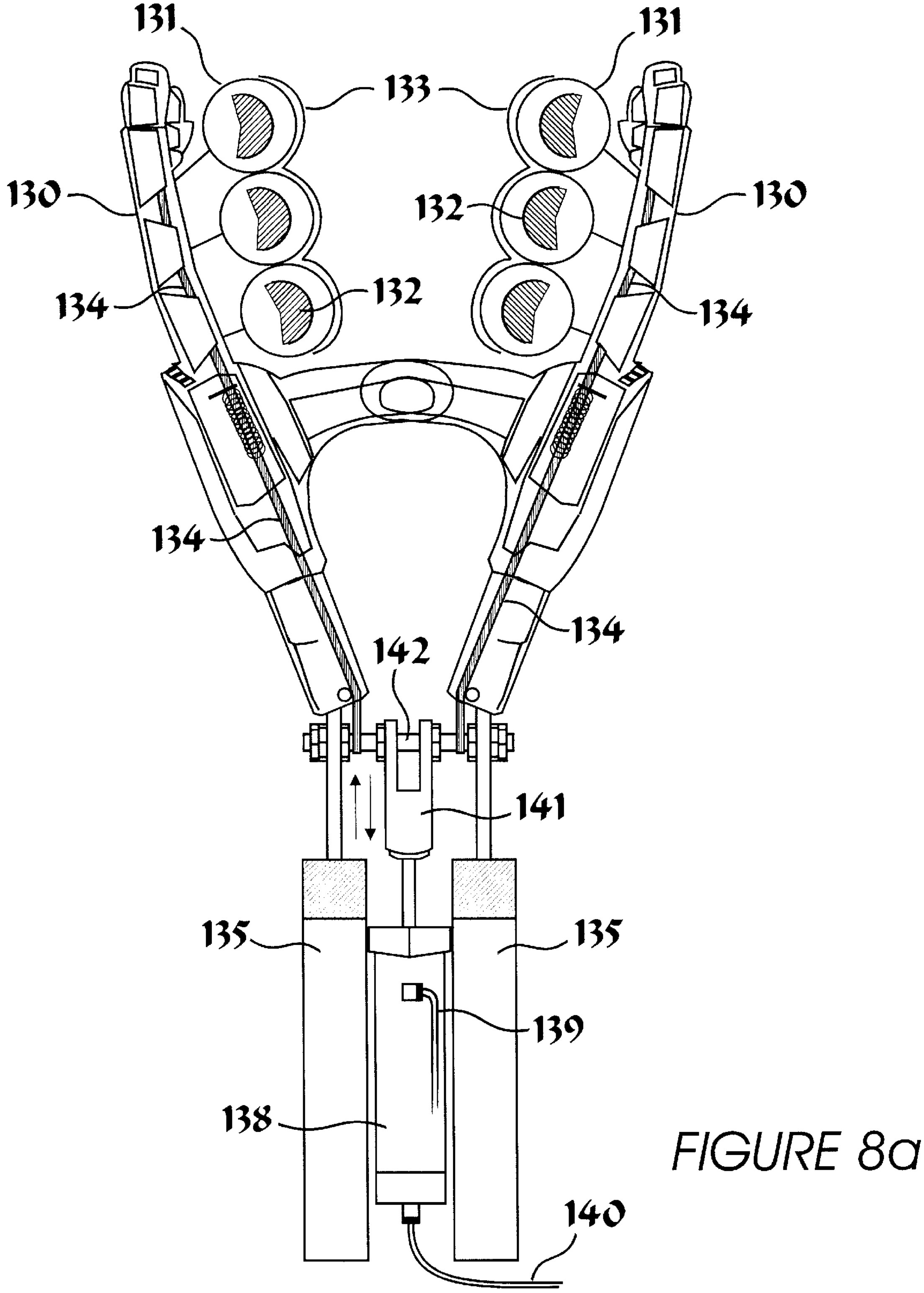
FIG. 8A is an exploded end view in partial cross section of an alternate embodiment for a flexible cable controlled massage gripper pair thereof.
Figure 8C:
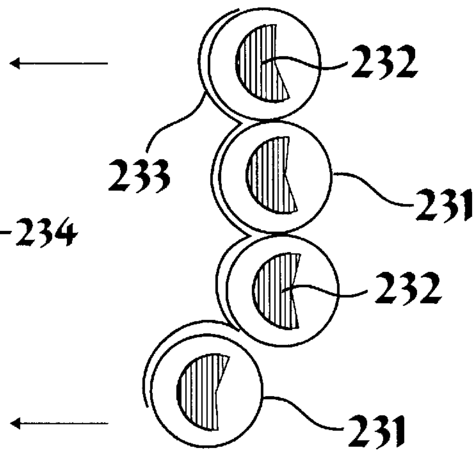
FIG. 8C is a close-up detail side view of the padding portion of the embodiment of FIG. 8B.
Figure 8B:
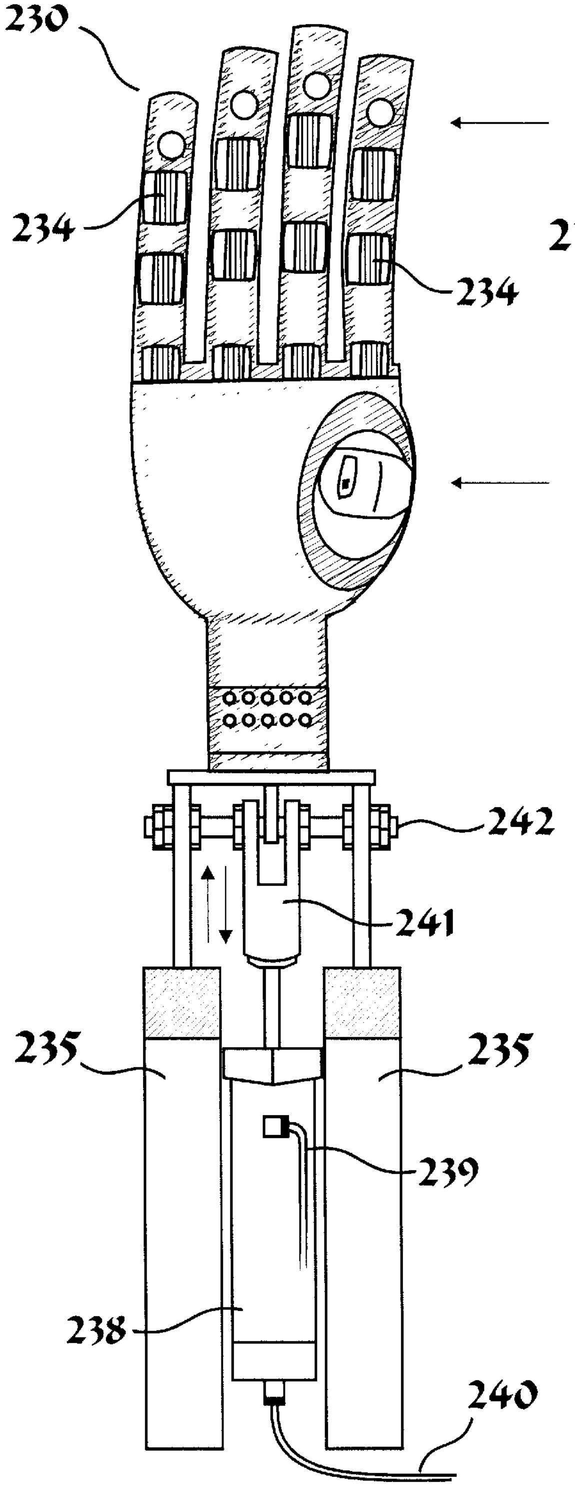
FIG. 8B is an end view in partial cross section of an alternate embodiment for a flexible controlled massage gripper with a moving half and a fixed half.

FIGS. 8A, 8B and 8C show alternate embodiments for massage grippers 130 and 230 respectively. In FIG. 8A, hinged grippers 130 are controlled by respective flexible cables 134 joined to distal ends of each gripper 130. Each gripper 130 is covered by compressed hard rubber balls 132 having super soft outer covers 131. Optional resistive heat wire 133 may be provided for heating grippers 130. Grippers 130 are mounted upon mount 135, and grippers 130 move by alternate up and down movement of cables 134 connected to connecting rods 142 attached to rod clevis 141 which is movable by pneumatic cylinder 138, powered by compressed air feed 140 to open grippers 130 and compressed air feed 139 to close grippers 130.

In FIGS. 8B and 8C, flexible cables 234 control movement of the movable half portion of massage gripper 230 against a fixed, non-moving half-portion. Flexible cables 234 joined to distal ends of each hinged gripper 230. Each gripper 230 is covered by compressed hard rubber balls 232 having super soft outer covers 231. Optional resistive heat wire 233 may be provided for heating grippers 230. Grippers 230 are mounted upon mount 235, and grippers 230 move by alternate up and down movement of cables 234 connected to connecting rods 242 attached to rod clevis 241, which is movable by pneumatic cylinder 238, powered by compressed air feed 240 to open grippers 230 and compressed air feed 239 to close grippers 230.

The side view of FIG. 9 shows a single pneumatic cylinder 38 operating both grippers 30 through rod clevis 41 and connecting rod 42. Cylinder 38 has pneumatic connection 39 to withdraw the rod and close the grippers and connection 40 to extend the piston rod to open the grippers.

Figure 10:
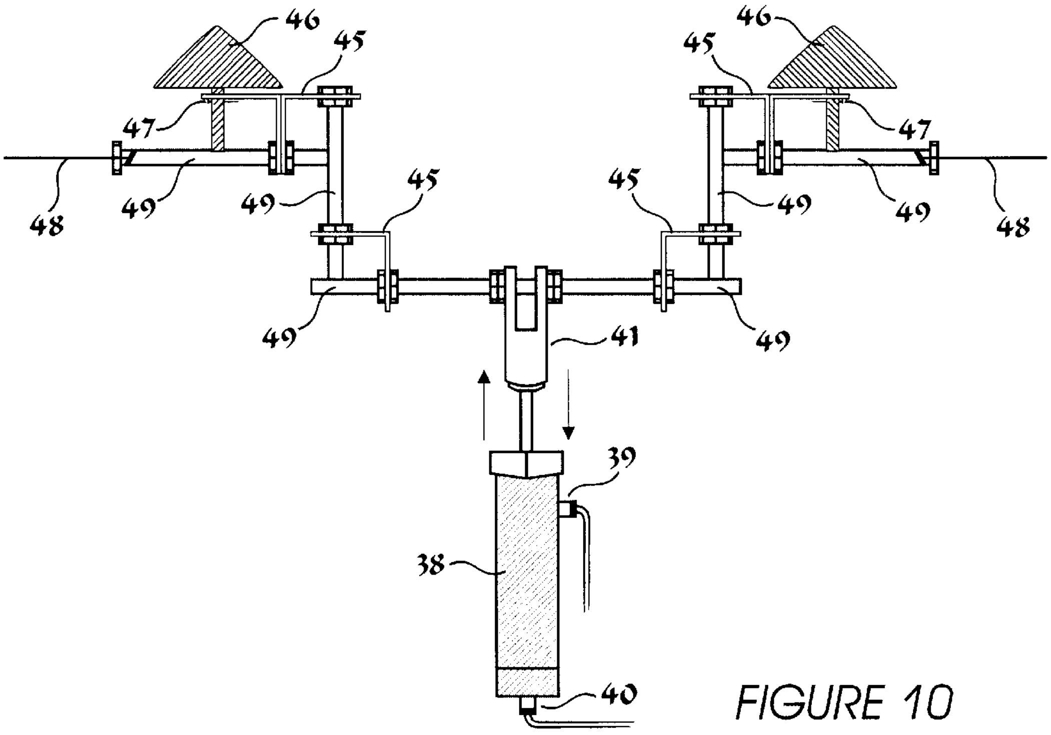
FIG. 10 is a side elevational view of the back massage subsystem thereof.

FIG. 10 is a detailed view of a "high-hat" subsystem used for back massage. A single pneumatic cylinder 38 is used to reciprocate vertically two conical wooden massage blocks 46 which are secured by locking pins 47. From cylinder 38 to blocks 46 is an intermediary linkage structure composed of clevis 41, several sections of threaded rod 49 and several "L" brackets 45 as shown. Elastic straps 48 secured to frame 2 are used to stabilize the assembly and to prevent pivoting.

Figure 11:
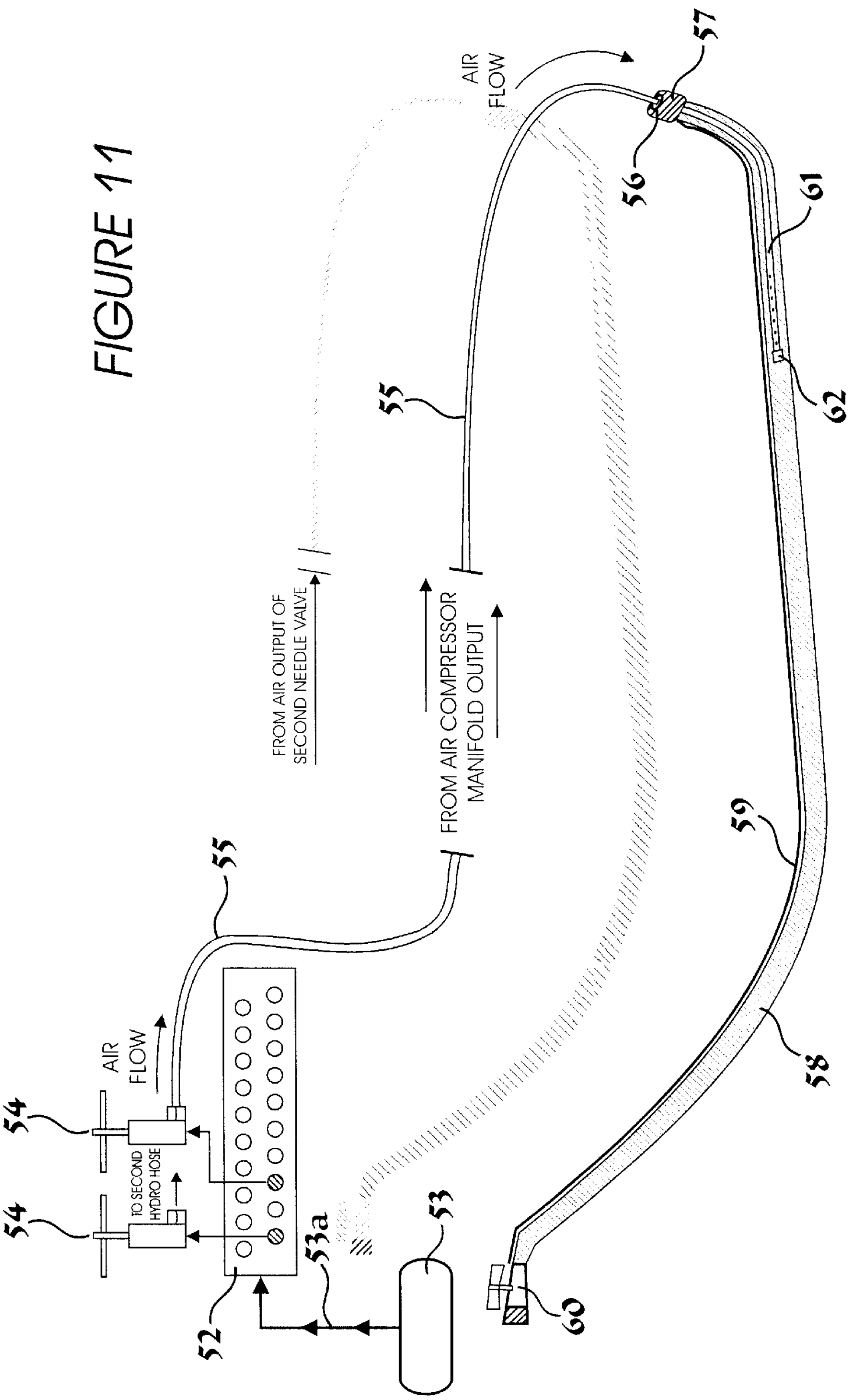
FIG. 11 is a side elevational view in partial cross section of the dry hydrotherapy sub-system thereof.

FIG. 11 shows one of the two optional dry hydrotherapy hose units. Unlike prior art dry hydrotherapy devices, no water is pumped nor heated for the present invention, wherein the dry hydrotherapy device can be used in conjunction with the whole body relaxation station 1, or with a limb-only embodiment with massage grippers, or as a dry hydrotherapy unit itself. Compressed air source 53 with compressed air line 53*a* from the compressor to manifold 52 supplies a constant source to needle valves 54 which regulate the flow to each hydrotherapy hose 58. Flexible tubing line 55 carries the regulated airflow through end cap 57 as sealed by grommet 56. Interior air hose 61 is perforated along its distal end and sealed with end plug 62. As air escapes into the water it causes bubbles and turbulence which the user can hear and feel. The effect can be optimized by judicious adjustment of both supply needle valve 54 and adjustable backpressure valve 60 at the elevated distal end of hydrotherapy hose 58. A resistive heat wire 59 is thermostatically controlled and gives the illusion of contact with warm flowing water.

Figure 12:
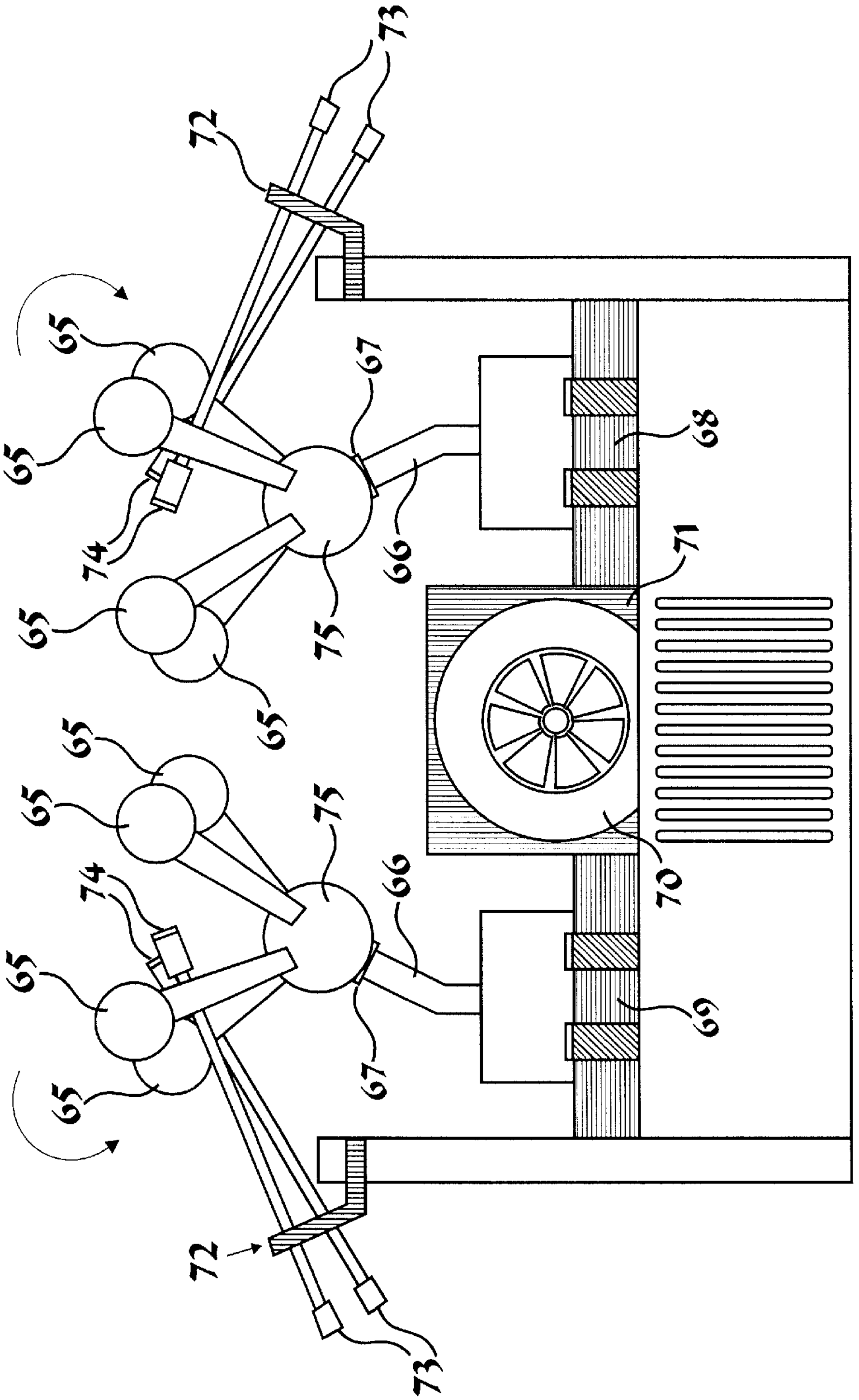
FIG. 12 is a side elevational view of the optional modified Shiatzu subsystem thereof.

FIG. 12 illustrates a preferable modified Shiatzu subsystem. Motor 71 with flywheel 70 drives left reduction gear assembly 69 with counterclockwise output and right reduction gear assembly 68 with clockwise output. Each of these gearbox outputs drives a similar apparatus including bent shaft 66 rotating freely in bearing 67 within central ball 75 with rigidly attached wooden ball massagers 65. To convert this orbital motion into the desired kneading motion of ball massagers 65, stops 74 mounted on rods 73 in mounts 72 are used to prevent full rotation and entanglement of massage balls 65.

Figure 13:
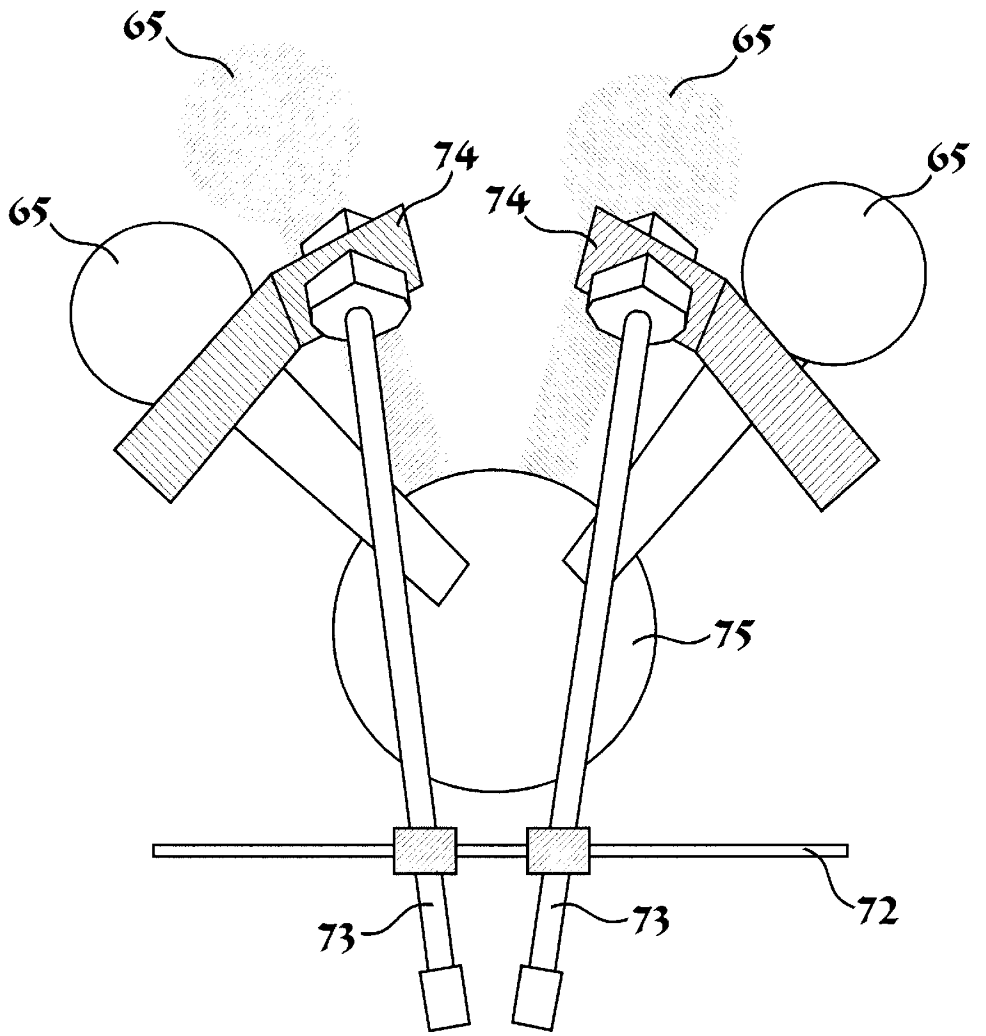
FIG. 13 is a side elevational detail view of the Shiatzu balls and stops thereof.

FIG. 13 is a detailed view from a different angle showing the interaction of stops 74 with balls 65 more clearly.

Figure 14:
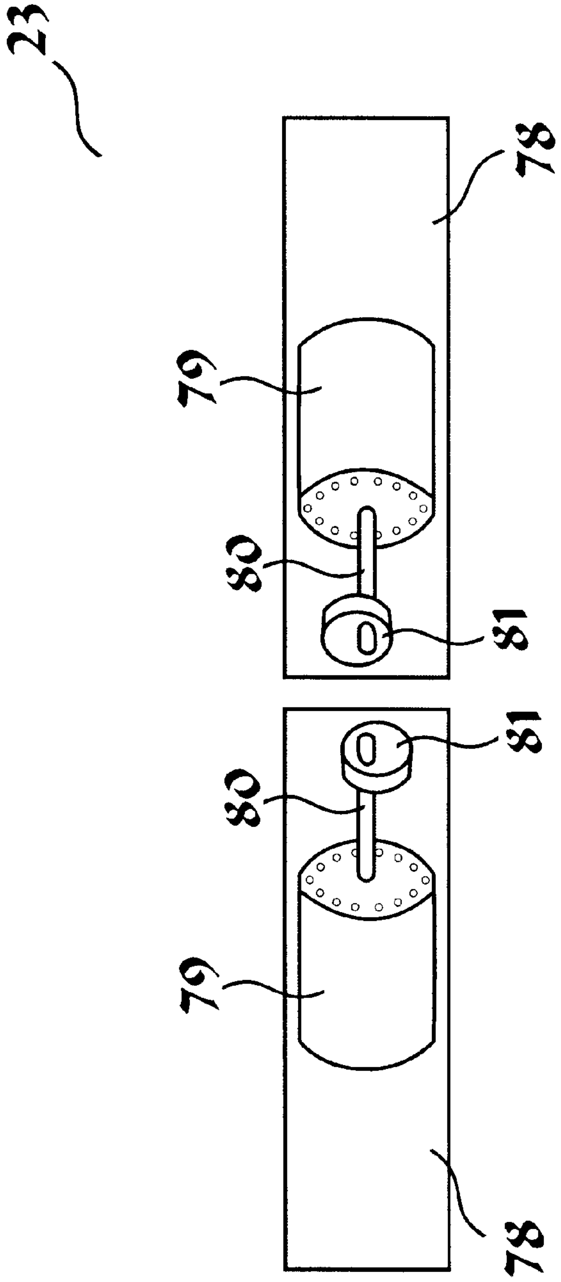
FIG. 14 is an isometric view of the optional dual motor vibratory-massage subsystem.

FIG. 14 is a dual motor vibratory-massage subsystem 23. It includes preferably two motors 79 with eccentrically mounted brass weights 81 mounted on each of their shafts 80. Each motor assembly is encased in a plastic housing 78 and any vibration is felt by the user in the lower back area. These are similar to enlarged versions of vibrators used in pagers as silent annunciators. By operating the motors at slightly different speeds, vibration frequencies at the rotation speed of each motor as well as the sum and difference vibration frequencies are generated as per normal harmonic motion theory. The difference frequency manifests as a slow wave and is particularly soothing.

A second embodiment for performing therapy of limbs-only is a self-contained portable limb-sized unit adaptable to use in home, hospital or a physical therapy center. It can be used for posttraumatic therapy of upper or lower arms or legs. It uses deep massage grippers and dry hydrotherapy subassemblies similar to those of the relaxation station 1. Because the objectives are different, electrical operation is used instead of pneumatic operation for the grippers. Control is via a small appliance type micro controller running dedicated microcode.

Figure 16:
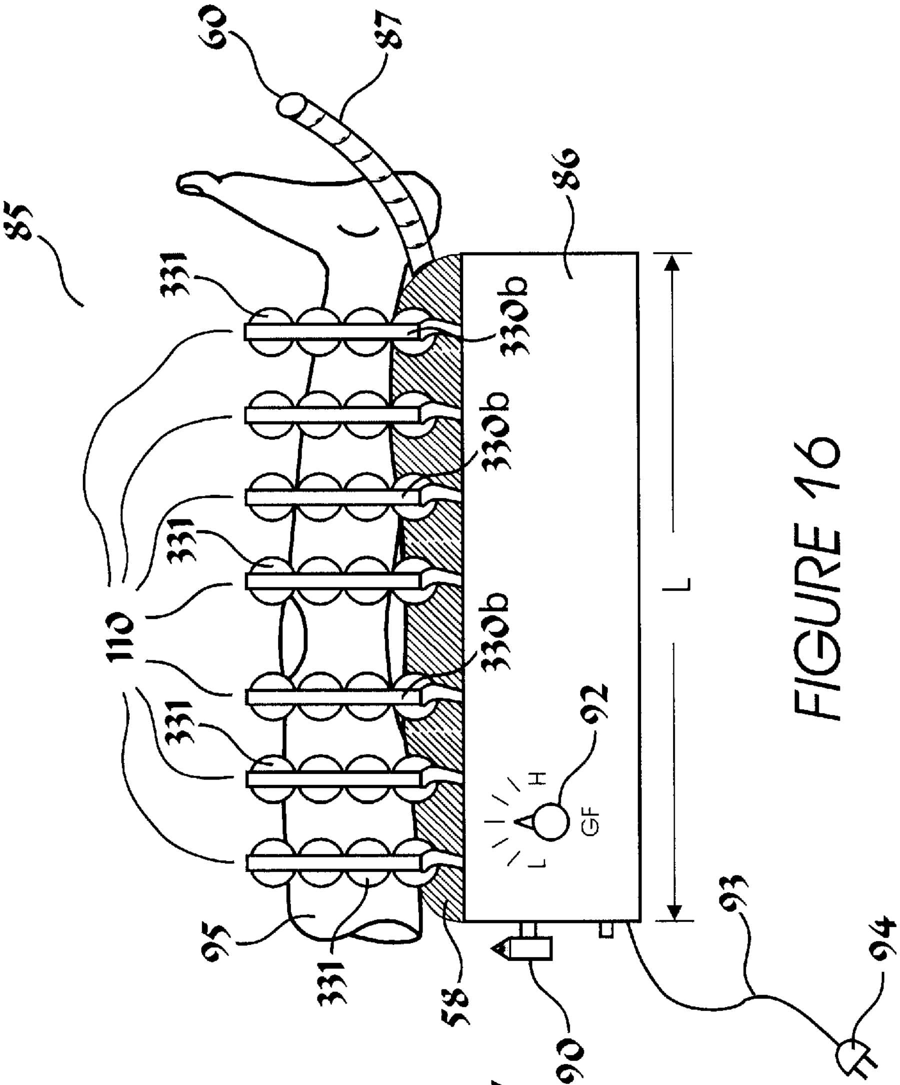
FIG. 16 is a side elevational view of the limb therapy unit as in FIG. 15.
Figure 15:
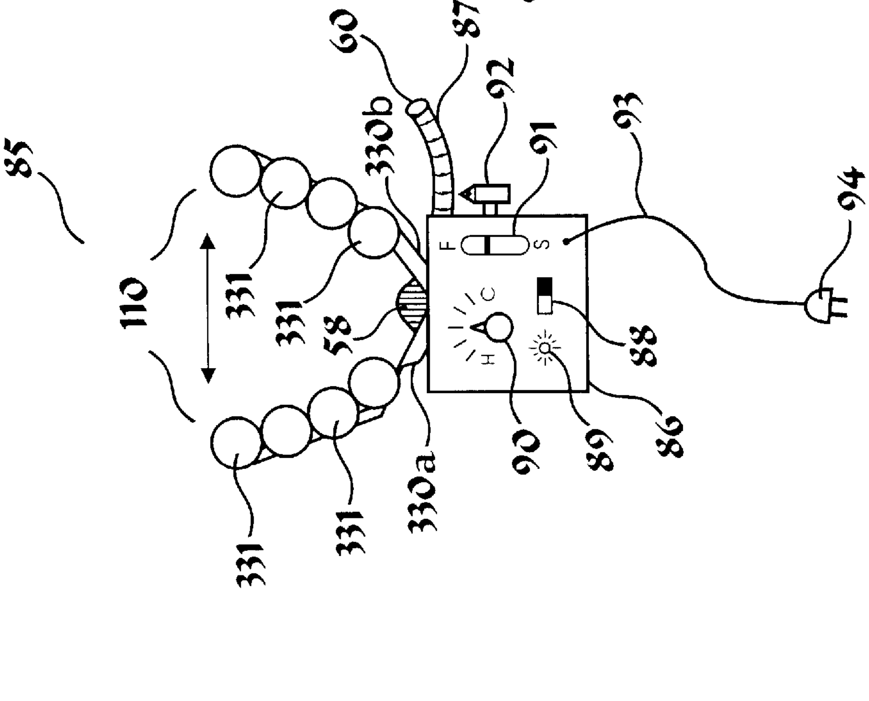
FIG. 15 is an end view of an alternate embodiment for a single limb therapy unit.

FIG. 15 shows an end view of limb therapy unit 85, FIG. 16 shows a side elevational view with a patient's leg 95 in place. A set of grippers 110, such as seven, for example, is illustrated with fewer or more being feasible for a longer or shorter unit (dimension L). Optional dry hydrotherapy hose 58 lies between grippers 110. Hose 58 has a raised adjustable (bendable) extension 87 with an adjustable backpressure valve 60. Limb unit 85 is built with a base housing 86 containing all of the controls and actuators. It is powered simply by plugging wall plug 94 on line cord 93 into a convenient wall outlet. The controls are simple to operate, an on/off switch 88, indicator lamp 89, temperature setting 90, speed setting linear potentiometer 91, and grip force adjustment 92. The sequence of the grippers is controlled by the micro controller to have a repetitive opening and closing wave motion.

FIGS. 15 and 16 show a plurality of massage gripper pairs 330 of complementary elongated jaw members 330*a*, 330*b* which each have a plurality of adjacent contact pads 331, such as balls. These contact pads 331 are positioned from a proximal end to an outer distal end of each respective complementary elongated jaw members 330*a*, 330*b*, so that they cradle and contact a user's limb at multiple skin contact points along limb 95. As noted before herein, and as shown in FIG. 16, the weight of limb 95 squeezes upon dry hydrotherapy hose 58, further spreading pulsation of air bubbles traveling within dry hydrotherapy hose 58.

Figure 17:
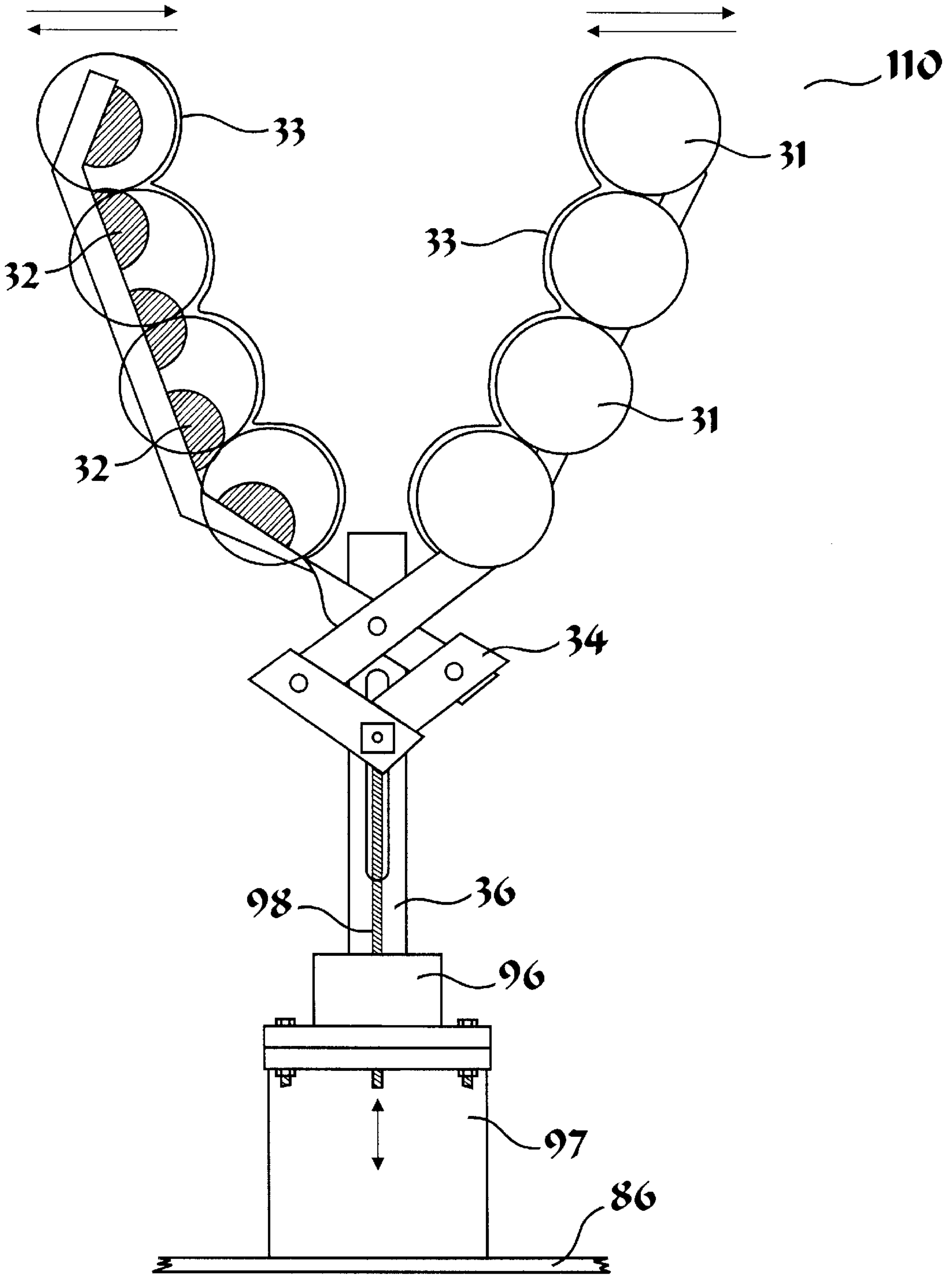
FIG. 17 is an end view in partial cross section of electrically operated gripper of the limb therapy unit, as in FIG. 15.

As can be seen in FIG. 17, the construction of grippers 110 is similar to those of the relaxation station. However, the drive system is by a lead screw type linear actuator 96 with one used for each gripper 110. Actuator 96 is a stepper motor type such as a Series 46000 from Haydon Switch and Instrument, Inc. of Waterbury, Conn. The maximum coil current permitted can regulate the peak force output of this motor. This type of motor can also be stalled without damage. These stepper motor features mean that the operational characteristics of the pneumatically driven relaxation station grippers can be closely simulated by these electrically driven grippers 110. Linear actuator 96 is mounted to stand 97 attached to housing 86. Lead screw 98 which passes through the center of actuator 96 drives ball and socket linkage block 99 up and down thereby opening or closing grippers 110. The balls 31 and 32 and the heat wire 33 are as described previously.

Figure 18:
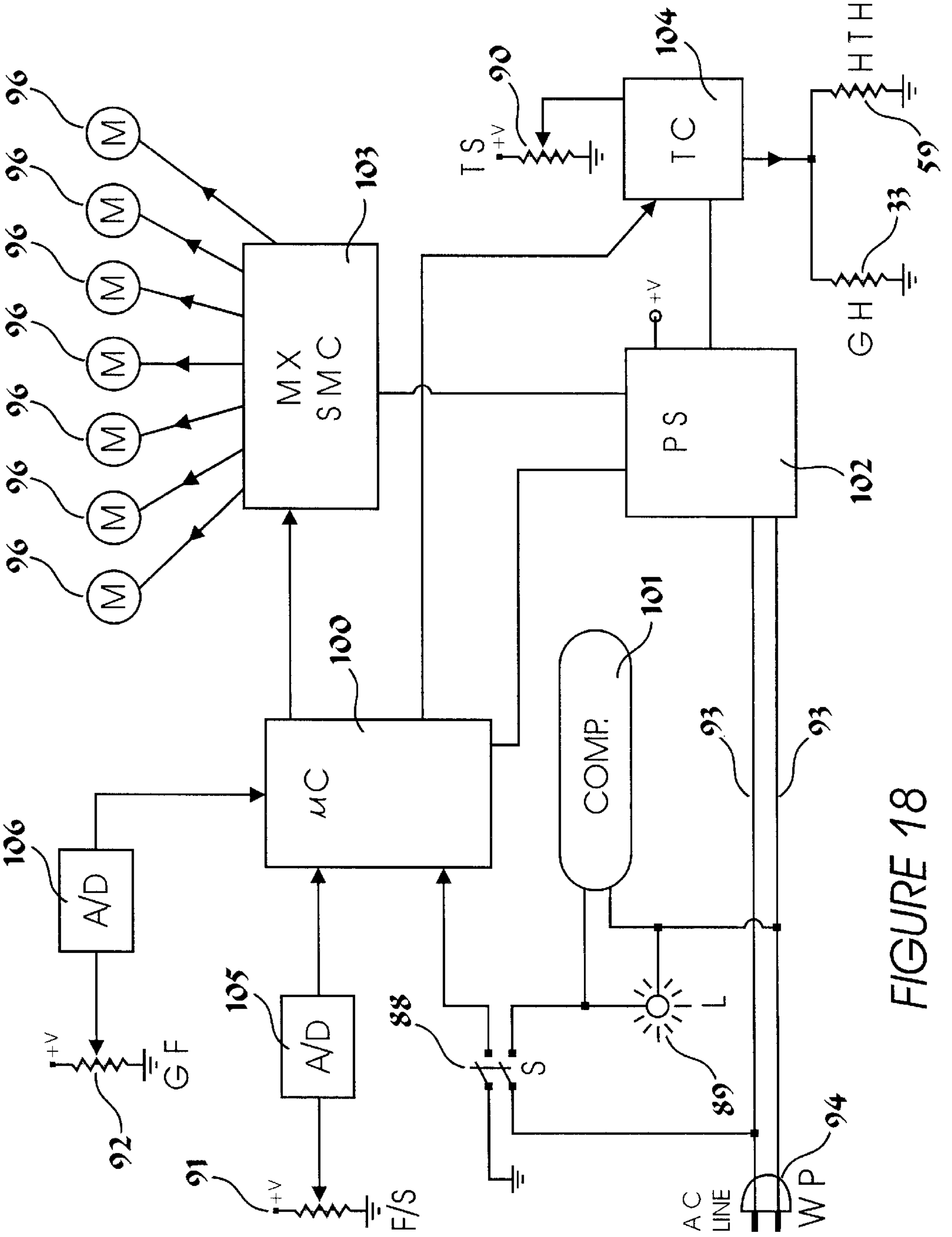
FIG. 18 is a block diagram of the limb therapy unit, as in FIG. 15; and, FIG. 19 is a flow chart of control software for the limb therapy unit as in FIG. 15.

FIG. 18 is a block diagram of the limb therapy unit 85. Power supply 102 provides power to micro controller 100, multiplexed stepper motor controller 103 and temperature controller 104. Compressor 101 is directly powered by 110–120 VAC through one leg of on/off switch 88 which also powers indicator lamp 89. Since compressor 101 only has to supply a low amount of low pressure air to bubble through the dry hydrotherapy hose, an aquarium aerator compressor will suffice, but for more robust effect, a small linear compressor such as a Linear ac 0102 model from Medo U.S.A., Inc. of Wood Dale, Ill. is preferred. A/D converter 105 and input to controller 100 converts the setting of speed control potentiometer 91. Similarly, grip force control 92 setting is input via A/D converter 106. The-heater temperature control setting is input directly from potentiometer 90 to the temperature controller which uses pulse width modulation (PWM) to regulate the heat output of gripper heaters 33 and hydrotherapy heater 59. Controller 100 can control the on/off nature of the temperature controller. The command protocol to the multiplexed stepper motor controller 103 involves the step frequency to all motors 96, the grip force maximum current to all motors 96 and direction signal to each specific motor 96 by address as per execution of the wave control algorithm.

Figure 19:
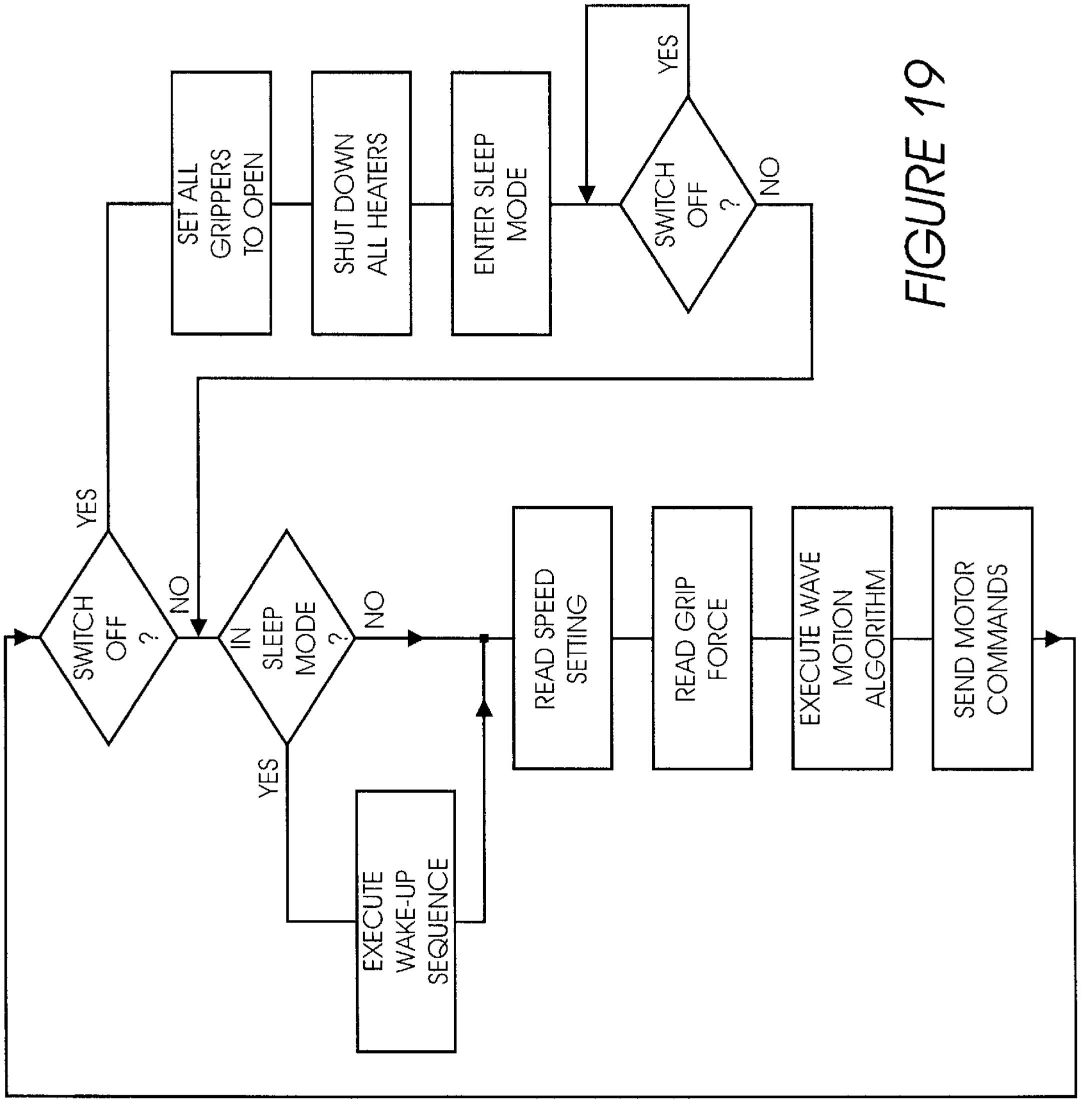

FIG. 19 is a high level flowchart of the control algorithm for the limb-only therapy unit. The controller is always powered as long as the unit is plugged in. It does enter sleep mode when switched off. The main control loop first monitors the on/off switch. If the switch is off, all grippers are set to full open, all heaters are shut off, and the controller enters sleep mode where it just monitors the setting of the on/off switch. Getting back to the main control loop, if the switch is on, but the controller is asleep, a wake-up sequence is executed. Then the speed setting and grip force settings are read and any changes are noted, the wave motion algorithm consisting of several timer loops is stepped through and any updates to the motor control settings are sent across to the multiplexed stepper motor controller 103. This loop is continuously executed unless interrupted by an "OFF" on/off switch setting.

It is further noted that other modifications may be made to the present invention, without departing from the scope of the invention, as noted in the appended Claims.

I claim:

1. A massage simulating station for treating at least one limb of a user, comprising:

a limb accommodating base housing having a limb resting surface for accommodating at least one limb of a user therein, a frame having a plurality of pairs of longitudinally extending, sequentially positioned massage grippers connected to and extending generally upward therefrom;

said pairs of massage grippers comprising complementary elongated jaw members projecting generally upward from said frame; each elongated jaw member further comprising a plurality of adjacent soft massage contact pads positioned from a proximal end of each said elongated jaw member to a distal outer end of each said elongated jaw member, said complementary elongated jaw members of said massage grippers being capable of moving reciprocally between an open and a closed position, said closed position cradling and contacting the limb of a user at multiple skin contact points thereof, said massage grippers having motive means for producing movement between said open and said closed positions;

each said massage gripper elongated jaw member respectively having attached thereon said plurality of soft massage contact pads for contacting and massaging the limb of a user, at said multiple skin contact points.

2. The limb massage simulating station of claim 1, wherein said motive means for producing movement of said plurality of pairs of elongated jaw members of said massage grippers between said open and said closed positions being compressed air dispenser.

3. The limb massage simulating station as in claim 1, wherein each said soft massage contact pad comprises a super-soft outer shell surrounding and attached to a relatively harder resilient inner liner, said inner liner being in turn attached to each said elongated jaw member.

4. The limb massage simulating station of claim 1, wherein said motive means for producing movement of said plurality of pairs of elongated jaw members of said massage grippers between said open and said closed positions being compressed air means; and each of said massage grippers further having said scissors extender means cooperating in concert with said compressed air means for producing movement of said pairs of complementary elongated jaw members of said plurality of pairs of massage grippers between said open and closed positions; and said motive means connected to said massage gripper elongated jaw members for producing clamping massage motions upon the limb.

5. The limb massage simulating station of claim 1 wherein said compressed air dispenser includes a compressor providing a pressurized source of air producing said clamping massage motions of said massage grippers, said motions of said massage grippers further modified by respective in-line flow control valves regulating a predetermined rate of air flow of said pressurized air, said predetermined rate of pressurized air flow controlling the rate of the opening and closing of each of said plurality of said pairs of elongated jaw members of said massage grippers.

6. The limb massage simulating station as in claim 1, wherein said motive means for said pairs of massage grippers are linear actuators powered by steppe; motors, said linear actuators driving ball and socket linkages to alternately open and close said pairs of elongated jaw members of said massage grippers.

* * * * *